(12) United States Patent
Mather et al.

(10) Patent No.: US 7,405,061 B2
(45) Date of Patent: Jul. 29, 2008

(54) ANTIGEN PIPA AND ANTIBODIES THAT BIND THERETO

(75) Inventors: Jennie P. Mather, Millbrae, CA (US); Ronghao Li, Millbrae, CA (US); Tony W. Liang, San Mateo, CA (US)

(73) Assignee: Raven biotechnologies, inc., South San Francisco, CA (US)

(*) Notice: Subject to any disclaimer, the term of this patent is extended or adjusted under 35 U.S.C. 154(b) by 441 days.

(21) Appl. No.: 10/713,248

(22) Filed: Nov. 13, 2003

(65) Prior Publication Data

US 2004/0171814 A1 Sep. 2, 2004

Related U.S. Application Data

(60) Provisional application No. 60/426,192, filed on Nov. 13, 2002.

(51) Int. Cl.
  C07K 16/30 (2006.01)
  C07K 16/28 (2006.01)
  A61K 39/395 (2006.01)
  C12P 21/04 (2006.01)
  C12N 5/10 (2006.01)
  C12N 5/12 (2006.01)
  C12N 15/63 (2006.01)
  C07H 21/02 (2006.01)
  C07H 21/04 (2006.01)
  C12N 15/13 (2006.01)

(52) U.S. Cl. .............. 435/70.21; 435/320.1; 435/330; 536/23.53; 424/130.1; 424/141.1; 424/143.1; 530/387.1; 530/388.1; 530/388.22

(58) Field of Classification Search ............... 530/387.1, 530/388.1, 388.22; 424/130.1, 141.1, 143.1; 536/23.53; 435/70.21, 320.1, 330
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,552,391 A | 9/1996 | Coutts et al. |
| 5,565,332 A | 10/1996 | Hoogenboom et al. |
| 5,580,717 A | 12/1996 | Dower et al. |
| 5,656,444 A | 8/1997 | Webb et al. |
| 5,665,570 A | 9/1997 | Yamagata et al. |
| 5,677,425 A | 10/1997 | Bodmer et al. |
| 5,733,743 A | 3/1998 | Johnson et al. |
| 5,760,185 A | 6/1998 | Kimachi et al. |
| 5,773,247 A | 6/1998 | Maeda et al. |
| 5,807,715 A | 9/1998 | Morrison et al. |
| 5,866,692 A | 2/1999 | Shitara et al. |
| 5,929,212 A | 7/1999 | Jolliffe et al. |
| 5,932,225 A | 8/1999 | Wallach et al. |
| 5,997,867 A | 12/1999 | Waldmann et al. |
| 6,054,297 A | 4/2000 | Carter et al. |
| 6,054,561 A | 4/2000 | Ring |
| 6,110,724 A | 8/2000 | Nakagomi et al. |
| 6,117,653 A | 9/2000 | Thoma |
| 6,180,377 B1 | 1/2001 | Morgan et al. |
| 6,221,644 B1 | 4/2001 | Berka et al. |
| 6,265,150 B1 | 7/2001 | Terstappen et al. |
| 6,331,415 B1 | 12/2001 | Cabilly et al. |
| 6,406,840 B1 | 6/2002 | Li et al. |
| 6,416,999 B1 | 7/2002 | Li et al. |
| 6,441,163 B1 | 8/2002 | Chari et al. |

FOREIGN PATENT DOCUMENTS

| | | |
|---|---|---|
| EP | 0 519 596 | 12/1992 |
| WO | WO 97/35614 | * 10/1997 |
| WO | WO-2004/043239 A2 | 5/2004 |

OTHER PUBLICATIONS

Bowie et al, Science, 247: 1306-1310, 1990.*
Burgess et al, J. Cell Biology, 111 : 2129-2138, 1990.*
Lazar et al, Molecular and Cellular Biology, 8: 1247-1252, 1988.*
Dickman, S., Science, 280: p. 1196-1197, 1998.*
Ianelli, C.J. et al, The Journal of Immunology, 159: 3910-3920, 1997.*
Aruffo, A. et al. (1987). "Molecular Cloning of a CD 28 cDNA by a High-Efficiency COS Cell Expression System," *Proc. Natl. Acad. Sci USA* 84:8573-8577.
Bird, R. E. et al. (1988). "Single-Chain Antigen-Binding Proteins," *Science* 242:423-426.
Brown, B. A et al. (1987). "Tumor-Specific Genetically Engineered Murine/Human Chimeric Monoclonal Antibody," *Cancer Res.* 47:3577-3583.
Carter, P. et al. (1992). "Humanization of an Anti-p185[HER2] Antibody for Human Cancer Therapy," *Proc. Nat. Acad. Sci USA* 89:4285-4289.
Co, M. S. et al. (1991). "Humanized Antibodies for Antiviral Therapy," *Proc. Nat. Acad. Sci USA* 88:2869-2873.
Co, M. S. et al. (1992). "Chimeric and Humanized Antibodies with Specificity for the CD33 Antigen," *J. Immunol.* 148(4):1149-1154.
Coligan, J.E. et al., eds (1991). "Isolation of Proteins Using Antibodies," In *Current Protocols in Immunology*, John Wiley & Sons, Inc., vol. 2, Supplement 18, pp. 8.2.1-8.2.9.
Daugherty, B. L. et al. (1991). "Polymerase Chain Reaction Facilitates the Cloning, CDR-grafting, and Rapid Expression of a Murine Monoclonal Antibody Directed Against the CD 18 Component of Leukocyte Integrins," *Nucl. Acids Res.* 19(9):2471-2476.
Dillman, R. O. et al. (1988). "Superiority of an Acid-Labile Daunorubicin-Monoclonal Antibody Immunoconjugate Compared to Free Drug," *Cancer Research* 48:6097-6102.
Gorman, S. D. et al. (1991). "Reshaping a Therapeutic CD4 Antibody," *Proc. Nat. Acad. Sci USA* 88:4181-4185.

(Continued)

*Primary Examiner*—Alana M. Harris
*Assistant Examiner*—Anne L Holleran
(74) *Attorney, Agent, or Firm*—Morrison & Foerster LLP

(57) ABSTRACT

Provided herein is disclosure about the identification and characterization of disease and cancer associated antigen PIPA. The invention also provides a family of monoclonal antibodies that bind to antigen PIPA, and methods of diagnosing and treating various human cancers and diseases that express PIPA.

42 Claims, 6 Drawing Sheets

OTHER PUBLICATIONS

Jones, P. T. et al. (1986). "Replacing the Complementarity-Determining Regions in a Human Antibody with Those from a Mouse," *Nature* 321:522-525.

Kettleborough, C. A et al. (1991). "Humanization of a Mouse Monoclonal Antibody by CDR-grafting: Importance of Framework Residues on Loop Conformation," *Protein Engineering* 4(7):773-783.

Fu, Q. et al. (Mar. 2001). "Carbohydrate-Directed Conjugation of Cobra Venom Factor to Antibody by Selective Derivatization of the Terminal Galactose Residues," *Bioconjugate Chemistry* 12(2):271-279.

Göttlinger, H.G. et al. (Jul. 16, 1986). "The Epithelial Cell Surface Antigen 17-1A, A Target for Antibody-Mediated Tumor Therapy: Its Biochemical Nature, Tissue Distribution and Recognition by Different Monoclonal Antibodies," *International Journal of Cancer* 38(1):47-53.

Kreitman, R.J. (Dec. 2001). "Toxin-Labeled Monoclonal Antibodies," *Current Pharmaceutical Biotechnology* 2(4):313-325.

Park, K.R. et al. (Aug. 2000). "Anti-CD9 Monoclonal Antibody-Stimulated Invasion of Endometrial Cancer Cell Lines in vitro: Possible Inhibitory Effect of CD9 in Endometrial Cancer Invasion," *Molecular Human Reproduction* 6(8):719-725.

Supplementary European Search Report mailed May 19, 2006, for EP Application No. 03786664.7 filed Nov. 13, 2003, three pages.

Zimmermann, S. et al. (1997). "A Novel Immunotoxin Recognising the Epithelial Glycoprotein-2 has Potent Antitumoural Activity on Chemotherapy-Resistant Lung Cancer," *Cancer Immunology and Immunotherapy* 44(1):1-9.

Kohler, G. et al. (1975). "Continuous Cultures of Fused Cells Secreting Antibody of Predefined Specificity," *Nature* 256:495-497.

Lobuglio, A. F. et al. (1989). "Mouse/Human Chimeric Monoclonal Antibody in Man: Kinetics and Immune Response," *Proc. Natl. Acad. Sci. USA* 86:4220-4224.

Lowe (1979). "An Introduction to Affinity Chromatography," *In Laboratory Techniques in Biochemistry and Molecular Biology*, North-Holland Publishing Company, Work, T. S. et al., eds., vol. 7 Part II, pp. 269-273 (Table of Contents Only).

Maeda, H. et al. (1991). "Construction of Reshaped Human Antibodies with HIV-Neutralizing Activity," *Human Antibodies Hybridomas* 2:124-134.

Mahato, R. I. et al. (1997). "Cationic Lipic-Based Gene Delivery Systems: Pharmaceutical Perspectives," *Pharm. Res.* 14(7):853-859.

Mangham D. C. et al. (1999). "A Novel Immunohistochemical Detection System Using Mirror Image Complementary Antibodies (MICA)," *Histopathology* 35(2):129-133.

Porath, J. et al. (1975). "Biospecific Affinity Chromatography and Related Methods," Chapter 2 In *The Proteins*, 3rd edition, Neurath, H. et al., eds. Academic Press, vol. 1 pp. 95-178.

Riechmann, L. et al. (1988). "Reshaping Human Antibodies for Therapy," *Nature* 332:323-327.

Shaw, D. R et al. (1987). "Characterization of a Mouse/Human Chimeric Monoclonal Antibody (17-1A) to a Colon Cancer Tumor-Associated Antigen," *J. Immunol.* 138:4534-4538.

Shen, W-C et al. (1981). "CIS-Aconityl Spacer Between Daunomycin and Macromolecular Carriers: A Model of Ph-Sensitive Linkage Releasing Drug From a Lysosomotropic Conjugate," *Biochem. Biophys Res. Commun* 102:1048-1054.

Stephan, J-P et al. (1999). "Distribution and Function of the Adhesion Molecule BEN During Rat Development," *Dev. Bio.* 212:264-277.

Stephan, J-P. et al. (1999). "Selective Cloning of Cell Surface Proteins Involved in Organ Development: Epithelial Glycoprotein Is Involved in Normal Epithelial Differentiation," *Endocrinology* 140(12):5841-5854.

Tempest, P. R. et al. (1991). "Reshaping a Human Monoclonal Antibody to Inhibit Human Respiratory Syncytial Virus Infection In Vivo," *Bio/Technology* 9:266-271.

Trouet, A. et al. (1982). "A Covalent Linkage Between Daunorubicin and Proteins That is Stable in Serum and Reversible by Lysosomal Hydrolases, as Required for a Lysosomotropic Drug-Carrier Conjugate: In Vitro and In Vivo Studies," *Proc. Natl. Acad. Sci.* 79:626-629.

Verhoeyen, M. et al. (1988). "Reshaping Human Antibodies: Grafting an Antilysozyme Activity," *Science* 239:1534-1536.

Weimer, L. M. et al. (2001). "Therapeutic Monoclonal Antibodies: General Principles," Chapter 20, Section 5 In *Cancer: Principles and Practice of Oncology*, 6th Edition, Freeman, Jr., Stuart, J. et al., eds. Lippincott Williams & Wilkins, pp. 495-508.

Wheatley, S. P. et al. (1998). "Indirect Immunofluorescence Microscopy in Cultured Cells," Chapter 18 In *Animal Cell Culture Methods*, Mather, J.P. and Barnes, eds, Academic Press, Inc. vol. 57, pp. 313-332.

Winter, G. et al. (1994). "Making Antibodies By Phage Display Technology," *Annual. Rev. Immunol.* 12:433-455.

Winter, G. et al. (1991). "Man-Made Antibodies," *Nature* 349:293-299.

Woodruff, T. K. (1998). "Cellular Localization of mRNA and Protein: In Situ Hybridization Histochemistry and in Situ Ligand Binding," Chapter 19 In *Animal Cell Culture Methods*, Mather, J.P. et al., eds, Academic Press, Inc. vol. 57, pp. 333-351.

Yang, H. M. et al. (1988). "Pharmacokinetics and Mechanism of Action of a Doxorubicin- Monoclonal Antibody 9.2.27 Conjugate Directed to a Human Melanoma Proteoglycan," *J. Natl. Can. Inst* 80:1154-1159.

International Search Report issued Jul. 12, 2005, for PCT Application No. PCT/US03/36134, filed Nov. 13, 2003, 5 pages.

Smith, G.M. et al. (1997). "Detection of a Soluble Form of the Leukocyte Surface Antigen CD48 in Plasma and its Elevation in Patients with Lymphoid Leukemias and Arthritis," *Journal of Clinical Immunology* 17(6):502-509.

* cited by examiner

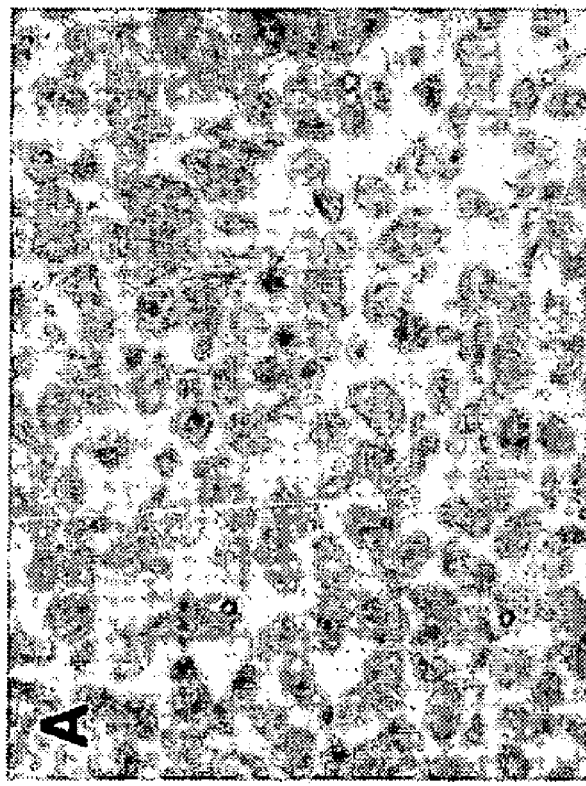
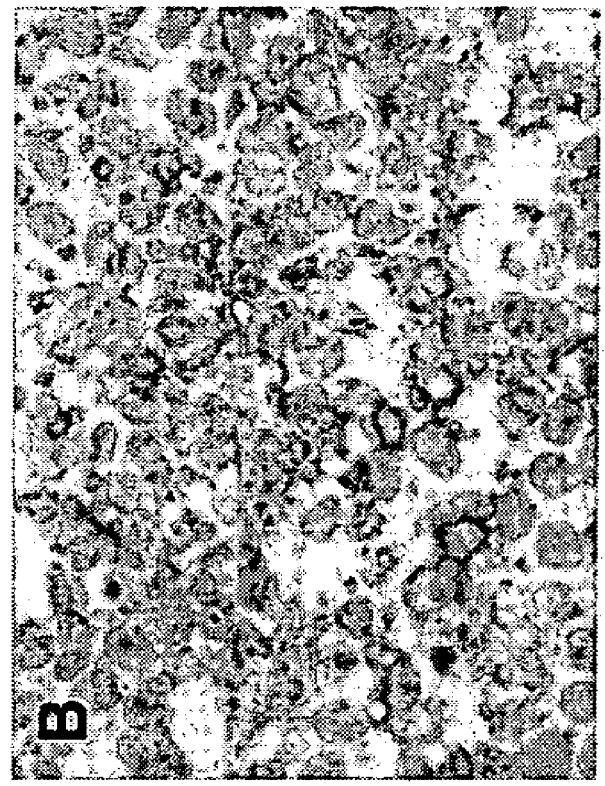
Figure 2

A. PIP Heavy chain variable region
gatgtgcagcttcaggagtcaggacctgacctggtgaaaccttctcagtcagtttcactcacctgcactgtcactggctactccatc
accagtggttatggctggcactggatccggcagtttccaggaaataaactggaatggatgggctgcatacactacagtggtagc
actaactacaacccatctctcaaaagtcgaatctctgtcactcgagacacatccaagaaccagttcttcctgcagttgaattctgtga
ctactgaggacacagccacatattactgtgcaagaagggaatatggtaactatgctatggactactggggtcaaggaacctcagt
caccgtctcctcag (SEQ ID NO:2)

DVQLQESGPDLVKPSQSVSLTCTVTGYSITSGYGWHWIRQFPGNKLEWMGCIHY
SGSTNYNPSLKSRISVTRDTSKNQFFLQLNSVTTEDTATYYCARREYGNYAMDY
WGQGTS VTVSS (SEQ ID NO:3)

B. PIP Heavy chain native signal sequence
atgagagtgctgattcttttgtgcctgttcacagcctttcctggtatcctgtct (SEQ ID NO:4)

MRVLILLCLFTAFPGILS (SEQ ID NO:5)

C. PIP Light chain variable region
gacattgtgatgacacagtctccatcctccctgagtgtgtcagcaggagagaaggtcactatgagctgcaagtccagtcagagtc
tgttaaacagtggaaatcaaaagaactacttggcctggtaccagcagaaaccagggcagcctcctaaactgttgatctacgggg
catccactagggaatctggggtccctgatcgcttcacaggcagtggatctggaaccgatttcactcttaccatcagcagtgtgcag
gctgaagacctggcagtttattactgtcagaatgatcatagttatccattcacgttcggctcggggacaaagttggaattaaaac
(SEQ ID NO:6)

DVQLQESGPDLVKPSQSVSLTCTVTGYSITSGYGWHWIRQFPGNKLEWMGCIHY
SGSTNYNPSLKSRISVTRDTSKNQFFLQLNSVTTEDTATYYCARREYGNYAMDY
WGQGTS VTVSS (SEQ ID NO:7)

D. PIP Light chain native signal sequence
atggaatcacagactcaggtcctcatctccttgctgttctgggtatctggtacctgtggg (SEQ ID NO:8)

MESQTQVLISLLFWVSGTCG (SEQ ID NO:9)

FIGURE 4

ANTIGEN PIPA AND ANTIBODIES THAT BIND THERETO

TECHNICAL FIELD

This invention is in the fields of biology and immunotherapy. More specifically, it concerns a novel disease and cancer-associated antigen, PIPA, and polyclonal and monoclonal antibodies and other polypeptides that bind to PIPA. The invention further provides methods for the diagnosis and/or treatment of a variety of human diseases and cancers associated with PIPA using antagonists, modulators and peptides that bind to PIPA, including anti-PIPA antibodies.

BACKGROUND OF THE INVENTION

In addition to their known uses in diagnostics, antibodies have been shown to be useful as therapeutic agents. For example, immunotherapy, or the use of antibodies for therapeutic purposes has been used in recent years to treat disease and cancer. Immunotherapy can be passive or active.

Passive immunotherapy involves the use of monoclonal antibodies in cancer treatments. See for example, *Cancer: Principles and Practice of Oncology*, 6$^{th}$ Edition (2001) Chapt. 20 pp. 495-508. These antibodies can have inherent therapeutic biological activity both by direct inhibition of diseased or tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are two examples of such therapeutics. Alternatively, antibodies can be used to make antibody conjugates where the antibody is linked to a toxic agent and directs that agent to the tumor by specifically binding to the tumor. Gemtuzumab ozogamicin is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alia, some molecular weights of target proteins: U.S. Pat. No. 6,054,561 (200 KD c-erbB-2 (Her2), and other unidentified antigens 40-200 KD in size) and U.S. Pat. No. 5,656,444 (50 KD and 55 KD, oncofetal protein). Examples of antibodies in clinical trials and/or approved treatments of solid tumors include: Trastuzumab (antigen: 180 kD, HER2/neu), Edrecolomab (antigen: 40-50 kD, Ep-CAM), Anti-human milk fat globules (HMFG1) (antigen>200 kD, HMW Mucin), Cetuximab (antigens: 150 kD and 170 kD, EGF receptor, Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the level of expression or in access of or activity of the antibody at these sites.

Another type of immunotherapy is active immunotherapy, or vaccination, with an antigen present on a specific pathogen, diseased cell or cancer, or a DNA construct that directs the expression of the antigen, which then evokes the immune response in the individual, ie., to induce the individual to actively produce antibodies against their own disease, pathogen or cancer. Active immunization has not been used as often as passive immunotherapy or immunotoxins.

Several models of disease (including cancer) progression have been suggested. Theories range from causation by a single infective/transforming event to the evolution of an increasingly "disease-like" or "cancer-like" tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up-regulated and/or over-expressed in tumor tissues. In such situations, some researchers have suggested that the over-expression is linked to the acquisition of malignancy, while others suggest that the over-expression is merely a marker of a trend along a path to an increasing disease state.

An ideal diagnostic and/or therapeutic antibody would be specific for an antigen present on a large number of diseased cells or cancers, but absent or present only at low levels on any normal tissue. The discovery, characterization, and isolation of a novel antigen that is specifically associated with disease(s) or cancer(s) would be useful in many ways. First, the antigen could be used to make monoclonal antibodies against the antigen. An antibody would ideally have biological activity against diseased or cancer cells and be able to recruit the immune system's response to foreign antigens. An antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radio-isotope, a toxin, or a chemotherapeutic agent or liposome containing a chemotherapeutic agent, with the conjugated form being biologically active by virtue of the antibody directing the toxin to the antigen-containing cells.

One aspect desirable for an ideal diagnostic and/or therapeutic antibody is the discovery and characterization of an antigen that is associated with a variety of cancers. There are few antigens that are expressed on a number of types of cancer (e.g., "pan-cancer" antigen) that have limited expression on non-cancerous cells. The isolation and purification of such an antigen would be useful for making antibodies (e.g., diagnostic or therapeutic) targeting the antigen. An antibody binding to the "pan-cancer" antigen could be able to target a variety of cancers found in different tissues in contrast to an antibody against an antigen associated with only one specific type of cancer. The antigen would also be useful for drug discovery (e.g., small molecules) and for further characterization of cellular regulation, growth, and differentiation.

What is needed are novel targets on the surface of diseased and/or cancer cells that may be used to diagnose and treat such diseases and/or cancers with antibodies and other agents which specifically recognize targets on the surface of cells. It is an object of this invention to identify targets on the surface of diseased and/or cancer cells that are limited in expression on normal tissues and cells. PIPA is such a target. It is another objective to provide novel compounds for use in the assay of PIPA, and for use as immunogens or for selecting anti-human PIPA antibodies.

As will be described in more detail below, the present inventors have discovered a novel antigen, which we refer to herein as PIPA, identified as the antigen target of the novel antagonists, modulators and antibodies provided herein.

SUMMARY OF THE INVENTION

In one aspect, the antigen hereinafter known as "PIPA," is provided. In another aspect, PIPA is bound by a monoclonal antibody PIP that is produced by a host cell (1hFT.1.6D4.1C8) that was deposited at the American Type Culture Collection (ATCC) on Apr. 9, 2002 (ATCC No. PTA-4220).

The invention provides for PIPA antagonists, modulators, polyclonal and monoclonal antibodies that bind to PIPA, which is expressed on a variety of human cancers.

In another aspect, the invention is an antibody or a polypeptide (which may or may not be an antibody) that binds specifically to PIPA. In one embodiment, the antibody is PIP (sometimes also referred to herein as "anti-PIPA"). In some embodiments, the antibody, modulator or polypeptide is a PIP equivalent antibody or a PIP equivalent polypeptide.

In another aspect, the invention is an antibody PIP that is produced by a host cell (1hFT.1.6D4.1C8; ATCC No. PTA-4220 or its progeny).

In yet another aspect, the invention is a method of generating a monoclonal antibody anti-PIPA reactive with diseased and/or cancerous cells comprising the steps of: (a) immunizing a host mammal with an immunogen; (b) obtaining lymphocytes from the mammal; (c) fusing lymphocytes with a myeloma cell line to produce a hybridoma; (d) culturing the hybridoma under conditions sufficient to produce monoclonal antibodies; (e) screening the antibodies to determine which antibodies bind to diseased and/or cancerous cells or cell lines; (f) optionally screening the antibodies to determine which antibodies bind to diseased and/or cancerous cells or cell lines with greater affinity than non-diseased and/or non-cancerous cells or cell lines; and (g) selecting the antibody that binds to the diseased and/or cancerous cells or cell lines but does not bind to non-diseased and/or non-cancerous cells or cell lines or that binds to diseased and/or cancerous cells or cell lines with greater affinity than non-diseased and/or cancerous cells or non-cancerous cell lines. In some embodiments, a PIPA modulator is selected by screening for binding that is at a similar level but in a different fashion between normal cells or cell lines and diseased and/or cancerous cells or cell lines. In some embodiments, the immunogen comprises human Mullerian duct-derived epithelial cells. In one embodiment, the monoclonal antibody that is generated by the method is PIP.

In another aspect, the invention is a modulator, antibody or a polypeptide (which may or may not be an antibody) that binds preferentially to the same epitope on PIPA as that which PIP binds preferentially.

In another aspect, the invention is an anti-PIPA antibody or a polypeptide or other PIPA modulator (which may or may not be an antibody) that competitively inhibits preferential binding of an anti-PIPA antibody to PIPA. In some embodiments, the invention is an antibody, modulator or a polypeptide (which may or may not be an antibody) that binds preferentially to the same or different epitope(s) on PIPA as other anti-PIPA antibodies.

In yet another aspect, the invention is a composition comprising PIPA bound by an antibody specific for an epitope of PIPA. In one embodiment, the antibody is PIP. In other embodiments, two or more anti-PIPA antibodies are administered, with such antibodies mapping to two or more different epitopes of PIPA. In some embodiments, the anti-PIPA antibody is linked to a therapeutic agent, a detectable label, or toxin.

In another aspect, the invention is a PIPA antibody comprising a fragment or a region of the antibody PIP. In one embodiment, the fragment is a light chain of the antibody PIP. In another embodiment, the fragment is a heavy chain of the antibody PIP. In yet another embodiment, the fragment contains one or more variable regions from a light chain and/or a heavy chain of the antibody PIP. In yet another embodiment, the fragment contains one or more complementarity determining regions (CDRs) from a light chain and/or a heavy chain of the antibody PIP.

In another aspect, the invention provides polypeptides (which may or may not be antibodies) comprising any of the following: a) one or more CDRs from either the light chain or the heavy chain; b) three CDRs from the light chain; c) three CDRs from the heavy chain; d) three CDRs from the light chain and three CDRs from the heavy chain; e) the light chain variable region; f) the heavy chain variable region of the antibody PIP.

In another aspect, the invention is a humanized antibody derived from murine PIP. In some embodiments, the humanized antibody comprises one or more CDRs of the antibody PIP. In another aspect, the invention provides a humanized antibody that binds to the same epitope(s) as antibody murine PIP. Generally, a humanized PIP antibody of the invention comprises one or more (one, two, three, four, five, six) CDRs that are the same and/or derived from the CDR(s) of antibody PIP. In another aspect, the invention provides a human antibody that binds to the same epitope(s) on PIPA as antibody PIP.

In another aspect, the invention is a chimeric antibody comprising variable regions derived from variable regions of a heavy chain and a light chain of antibody PIP and constant regions derived from constant regions of a heavy chain and a light chain of a human antibody.

In yet another aspect, the invention is a host cell (1hFT.1.6D4.1C8; ATCC no. PTA-4220), or progeny thereof, which produces monoclonal antibody PIP. In another aspect, the invention is an isolated polynucleotide that encodes for antibody PIP that is produced by, a host cell with a deposit number of ATCC No. PTA-4220, or progeny thereof. In another aspect, the invention provides polynucleotides encoding any of the antibodies (including antibody fragments) as well as any other polypeptides described herein.

Other PIPA modulators encompassed by this invention are described in more detail in following sections of this specification.

In yet another aspect, the invention is a complex of PIPA bound by any of the antibodies or polypeptides described herein.

In another aspect, the invention is a complex of a cancer cell expressing PIPA bound by any of the antibodies or polypeptides described herein. In some embodiments, the cancer cell is an ovarian or colon cancer cell.

In another aspect, the invention is a complex of an epitope that PIP preferentially binds bound by any antibody or polypeptide described herein.

In another aspect, the invention is a pharmaceutical composition comprising any of the polypeptides (including any of the antibodies such as antibody PIP) or polynucleotides described herein, such as pharmaceutical compositions comprising the antibody PIP, the antibody PIP linked to a therapeutic agent, the antibody PIP linked to a toxin, an antibody comprising a fragment of the antibody PIP, a humanized antibody of the antibody PIP, a chimeric antibody comprising variable regions derived from variable regions of the antibody PIP and constant regions derived from constant regions of a human antibody, or a human antibody with one or more properties of the antibody PIP, and a pharmaceutically acceptable excipient.

In another aspect, the invention is a method of generating antibody PIP comprising culturing a host cell (ATCC No. PTA-4220), or progeny thereof, under conditions that allow production of the antibody PIP, and purifying the antibody PIP.

In one aspect, the invention is a composition comprising an anti-PIPA antibody bound to PIPA on a diseased or cancerous cell. In preferred embodiments, the cancer ell is selected from a group consisting of ovarian, lung, prostate, pancreatic, colon, and breast cancer cells. In some embodiments, the cancer cell is isolated. In some embodiments, the cancer cell is in a biological sample. Generally, the biological sample is individual, such as a human.

In another aspect, the invention is a method of diagnosing disease in an individual by detecting PIPA on cells from the individual, particularly diseases or disorders associated with inflammatory or autoimmune responses in individuals. In other aspects of the invention, methods are provided for modulating inflammatory or autoimmune responses in individuals. Diseases and conditions resulting from inflammation and autoimmune disorders that may be subject to treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia, and acute leukocyte-mediated lung injury.

Still other indications for therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas, and bone marrow. Perhaps the principal outstanding problem is the lack of satisfactory agents for inducing immunotolerance in the recipient to the transplanted allograft or organ. When allogenic cells or organs are transplanted into a host (i.e. the donor and donee are different individuals from the same species), the host immune system is likely to mount an immune response to foreign antigens in the transplant (host-versus-graft disease) leading to destruction of the transplanted tissue.

In yet another aspect, the invention is a method of diagnosing cancer in an individual by detecting antigen PIPA on cells from the individual using the antibody PIP or any PIPA binding moiety (polypeptides, including, but not limited to, various antibodies and antibody derivatives) described herein. In some embodiments, the method involves detecting the level of PIPA expression from cells. The term "detection" as used herein includes qualitative and/or quantitative detection (measuring levels) with or without reference to a control.

In yet another aspect, the invention is a method of diagnosing cancer in an individual by detecting PIPA on or released from cells from the individual, wherein the cancer is selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumors, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In another aspect, the invention is a method for aiding diagnosis of cancer (such as, but not limited to, ovarian, lung, prostate, pancreatic, colon, uterine, or breast cancer) in an individual comprising determining the expression of PIPA in a biological sample from the individual. In some embodiments, the expression of PIPA is determined using an anti-PIPA antibody. In some embodiments, the method is detecting the level of PIPA expression from cells. The PIPA released from the cancer may contribute to elevated levels of PIPA or a portion thereof, being detectable in body fluids. In yet another aspect, the invention is a method of treating cancer by administering an effective amount of an antibody that binds to PIPA sufficient to reduce growth of cancerous cells. In some embodiments, the antibody is an anti-PIPA antibody, such as PIP. In certain embodiments, the cancerous cells are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochiomocytoma, pituitary tumors, prostate cancer, posterious unveal melanoma, rare hematologic disorders, renal metastatic cancer, rhabdoid tumors, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In yet another aspect, the invention is a method of inhibiting growth and/or proliferation of diseased or cancerous cells in an individual by administering to the individual an effective amount of a composition comprising an agent that binds specifically to antigen PIPA. In some embodiments, the agent comprises the antibody PIP, or any of the antibodies (including polypeptides) or polynucleotides embodiments described herein, including, but not limited to, the antibody PIP associated with a therapeutic agent, an antibody comprising a fragment or a region of the antibody PIP, a humanized antibody (generally, but not necessarily, comprising one or more CDRs of the antibody PIP), a chimeric antibody comprising variable regions derived from variable regions of the antibody PIP and constant regions derived from constant regions of a human antibody, or a human antibody with one or more properties of the antibody PIP.

In certain embodiments, cells capable of expressing PIPA, or cells capable of expression an anti-PIPA antibody or other modulator, are administered to an individual so that the individual's own body mediates the immune response. Local expression of PIPA in vivo may provoke an effective response within the individual. Similarly, local expression of cells capable of expression an anti-PIPA antibody or other modulator may result in desirable therapeutic benefits. Such methods of direct administration of whole cells to an individual are encompassed by this invention.

In yet another aspect, the invention is a method of delaying development of metastasis in an individual with cancer by administering an effective amount of a composition comprising an agent that binds specifically to antigen PIPA. In some embodiments, the agent comprises the antibody PIP, or any of the antibodies (including polypeptides) or polynucleotides embodiments described herein, including but not limited to the antibody PIP associated with a therapeutic agent, an antibody comprising a fragment or a region of the antibody PIP, a humanized antibody (generally, but not necessarily, comprising one or more CDRs of the antibody PIP), a chimeric antibody comprising variable regions derived from variable regions of the antibody PIP and constant regions derived from constant regions of a human antibody, or a human antibody with one or more properties of the antibody PIP.

In yet another aspect, the invention is a method of delivering a therapeutic agent (such as a toxin, radioactive compound, or chemotherapeutic agent) to cancerous cells in an individual by administering to the individual an effective amount of an agent that binds specifically to the antigen PIPA. Agents that bind specifically to the antigen PIPA include, but are not limited to, the antibody PIP, an antibody comprising a fragment or a region of the antibody PIP, or a humanized antibody (generally, but not necessarily, comprising one or more CDRs of the antibody PIP), a chimeric antibody comprising variable regions derived from variable regions of the antibody PIP and constant regions derived from constant regions of a human antibody, or a human antibody with one or more properties of the antibody PIP. In some embodiments, the cancerous cells are from breast, colon, lung, ovarian, pancreatic, prostate, renal, or uterine cancer. Accordingly, in particular embodiments, the invention provides methods of inhibiting growth and/or proliferation of ovarian or colon cancer cells by delivering the therapeutic agent to those cancer cells.

In yet another aspect, the invention is a method of modulating an immune system in an individual by administering to the individual an agent that binds specifically to antigen PIPA in an amount sufficient to induce an immune response against diseased or cancerous cells expressing antigen PIPA.

In yet another aspect, the invention is a method of modulating an immune system in an individual by administering to the individual an effective amount of the antigen PIPA sufficient to induce an active immune response to diseased or cancerous cells expressing antigen PIPA. In one embodiment, the antigen is administered with an adjuvant.

In yet another aspect, the invention is a method of modulating an immune system in an individual by administering to the individual an effective amount of a nucleic acid sequence encoding the antigen PIPA sufficient to induce an active immune response to diseased or cancerous cells expressing antigen PIPA. In one embodiment, the antigen is administered with an adjuvant.

In yet another aspect, the invention is a method for screening an agent which binds specifically to antigen PIPA by contacting cells expressing PIPA with said agent and assessing the binding of said agent in a detection assay.

In another aspect, the invention provides kits comprising any one or more of the compositions described herein. These kits, generally in suitable packaging and provided with appropriate instructions, are useful for any of the methods described herein.

BRIEF DESCRIPTION OF THE DRAWINGS

FIG. 2 shows photographs of immunohistochemical staining of the colon cancer cell line HT-29 in frozen section in both the absence (FIG. 2A) and presence (FIG. 2B) of PIP antibody.

FIG. 4 shows the nucleic acid sequence (SEQ ID NO:6) of the variable region of the light chain (mouse IgG1, kappa) of the anti-PIPA monoclonal antibody PIP, including the native signal sequence (SEQ ID NO:8). Corresponding protein translation is included below the DNA sequence (SEQ ID NO:7 and SEQ ID NO:9). Also included is the nucleic acid sequence (SEQ ID NO:2) of the variable region of the heavy chain of the anti-PIPA monoclonal antibody PIP, including the native signal sequence (SEQ ID NO:4). The corresponding protein translation is included below the DNA sequence (SEQ ID NO:3 and SEQ ID NO:5).

DETAILED DESCRIPTION OF THE INVENTION

Figure 1:
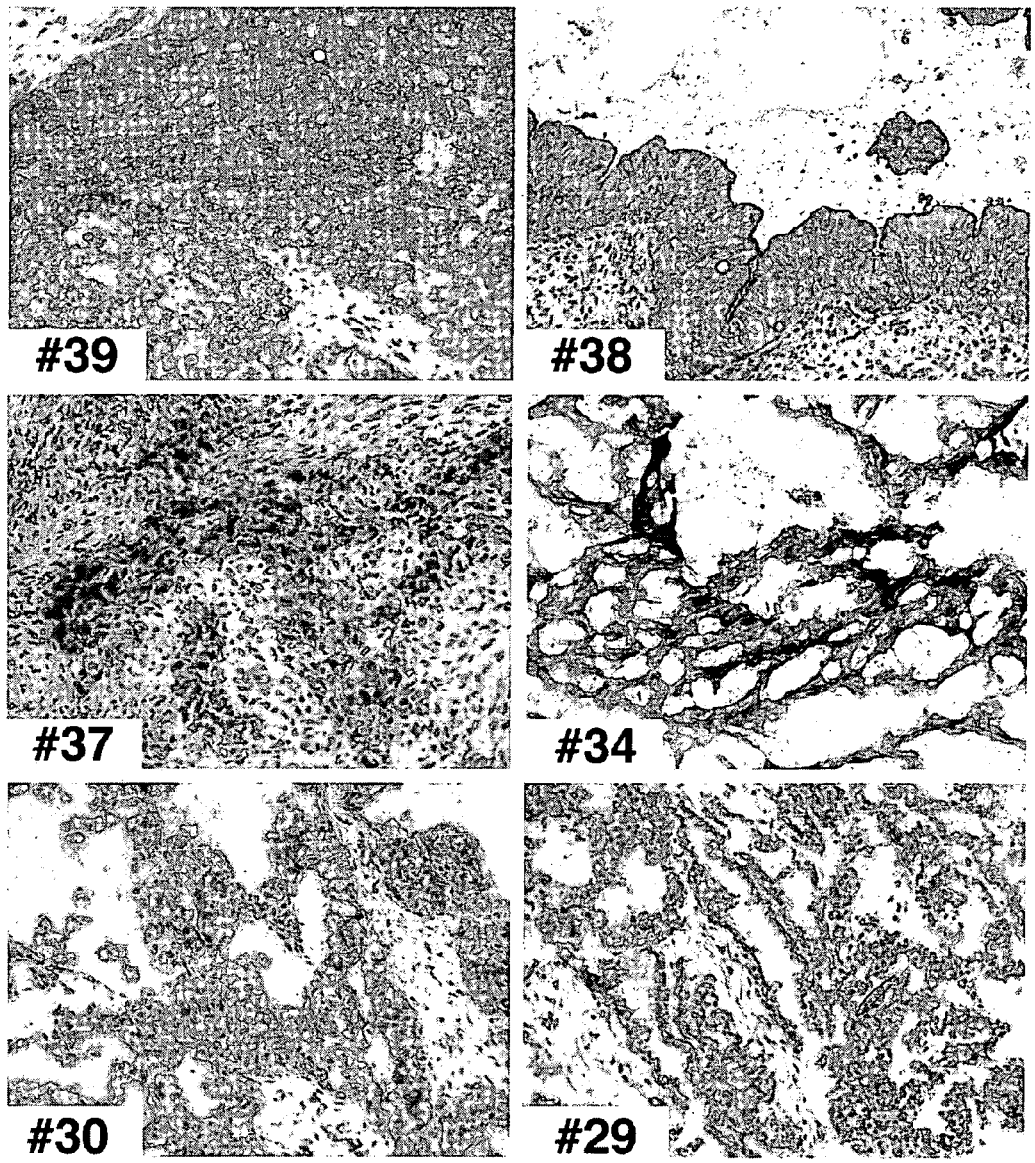
FIG. 1 shows photographs of immunohistochemical staining of cancerous cells in multiple ovarian cancer tissue samples.

The invention disclosed herein provides the identification and characterization of a disease and/or cancer-associated antigen PIPA, and also provides methods of making and using antibodies and polypeptides that bind to PIPA. Methods are provided for methods making and using these antibodies and polypeptides to diagnose and treat various diseases human cancers associated with expression and/or over-expression of PIPA.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology (C. A. Janeway and P. Travers*, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

"PIPA" refers to that novel polypeptide antigen with a glycosylated molecular weight of approximately 45 kD to 50 kD (+/−10% on a 4-20% Tris-glycine SDS-PAGE (ie., denaturing gradient) gel), against which the antibodies and modulators of the present invention are directed. The antigen PIPA is a cell surface, GPI-linked, glycoprotein bound by PIP and is present on several types of carcinomas and on other cells such as ovarian and colon cells. The antigen may have more than one different epitope. It is currently believed that PIPA may be over-expressed in certain cancer cells in comparison to their normal tissue counterparts.

In one embodiment, the epitope is an antigen or part of an antigen that is bound by the monoclonal antibody PIP. In a preferred embodiment, the epitope is an antigen or part of an antigen that is a glycosylated protein. In a particularly preferred embodiment, the epitope is an antigen or part of an antigen that is a GPI-linked glycosylated protein. In another particularly preferred embodiment, the epitope is an antigen or part of an antigen that encompasses both the glycosylated protein and the post-translational modification.

In another embodiment, the epitope is a glycotope present on the antigen or a part of the antigen. The glycotope can include but is not limited to mannose, N-acetylglucosamine, N-acetylneuraminic acid (sialic acid), galactose, and glucose.

These post-translational modifications can include, but are not limited to glycosylation, phosphorylation, sialation, sulfation, and conformational changes due to binding of divalent cations, In a particularly preferred embodiment, the glycosylation can include, but are not limited to N-linked glycosylation, O-linked glycosylation, complex oligosaccharides, and high mannose oligosaccharides.

Agonists, antagonists, and other modulators of PIPA function are expressly included within the scope of this invention. These agonists, antagonists and modulators are polypeptides that comprise one or more of the antigenic determinant sites in PIPA, or comprise one or more fragments of such sites, variants of such sites, or peptidomimetics of such sites. These agonistic, antagonistic, and PIPA modulatory compounds are provided in linear or cyclized form, and optionally comprise at least one amino acid residue that is not commonly found in nature or at least one amide isostere. These compounds may be glycosylated.

More specifically, the terms "PIPA agonist", antagonist" or "modulator" as used herein are defined as any compound that (1) is capable of disrupting or blocking the interaction with human PIPA and its native ligands or an anti-PIPA antibody; (2) is capable of binding to human PIPA and its native ligands or an anti-PIPA antibody; (3) contains an antigenic site that can be used in the raising of antibodies-capable of binding to human PIPA and its native ligands or an anti-PIPA antibody; (4) contains an antigenic site that can be used in the screening of antibodies capable of binding to human PIPA and its native ligands or an anti-PIPA antibody; (5) contains an antigenic site that can be used in the raising of antibodies capable of disrupting or blocking the interaction between human PIPA and its native ligands or an anti-PIPA antibody; (6) contains an antigenic site that can be used in the screening of antibodies capable of disrupting or blocking the interaction between human PIPA and its native ligands or an anti-PIPA antibody.

PIPA agonists, antagonists and modulators include PIPA variants, PIPA peptide antagonists, peptidomimetics, and small molecules, anti-PIPA antibodies and immunoglobulin variants, nucleic acid and amino acid variants of human PIPA including substitution, deletion, and addition variants, or any combination thereof, and chimeric immunoglobulins. Such compounds are used herein interchangeably, and are meant to include, but are not limited to, peptides, nucleic acids, carbohydrates, small organic molecules, natural product extract libraries and any other molecules (including but not limited to, chemicals, metals and organometallic compounds).

The PIPA agonists, antagonists and modulators of this invention are based on the inventors' identification of the identification of the PIPA domains involved in the binding of human PIPA to its native ligands or anti-PIPA antibodies. Thus, the invention provides PIPA agonists, antagonists and modulators with molecular structures that duplicate or mimic one or more of the anti-PIPA binding domains of human PIPA.

The binding domains of this invention can be considered as a "druggable targets," "druggable regions" and "druggable target regions"; such terms may be used herein interchangeably to refer to a region on the three dimensional structure of a polypeptide, carbohydate, or complex that is a likely target for binding a PIPA modulator. A druggable region generally refers to a region where several amino acids of a polypeptide or complex, would be capable of interacting with a modulator. In certain embodiments, the druggable region is that region where post-translational modifications (such as glycosylation) influence the conformation of the amino acids of the polypeptide or complex. Exemplary druggable regions include binding pockets, enzymatic active sites, surface grooves or contours or surfaces of a polypeptide or complex that are capable of participating in interactions with another molecule.

As used herein, the term "PIPA variant" denotes any amino acid variant of human PIPA, including nucleic acid or amino acid substitution, deletion, and addition variants, or any combination thereof The definition encompasses chimeric molecules such as human PIPA/non-human chimeras and other hybrid molecules. Also included in the definition is any fragment of a PIPA variant molecule that comprises the variant or hybrid region(s) of the molecule.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, humanized antibodies, chimeric antibodies, and any other modified configuration of the immunoglobulin molecule that comprises an antigen recognition site of the required specificity.

A "monoclonal antibody" refers to a homogeneous antibody population wherein the monoclonal antibody is comprised of amino acids (naturally occurring and/or non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody".

"Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immuno response to the foreign variable region remains (LoBuglio, A. F. et. al., (1989) Proc Natl Acad Sci USA 86:4220-4224). Another approach focuses not only on providing human-derived constant regions, but modifying the variable regions as well so as to reshape them as closely as possible to human form. It is known that the variable regions of both heavy and light chains contain three-complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al., (1988) Science 239:1534-1536; Kettleborough, C. A., et al., (1991) Protein Engineering 4:773-783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S., et al., (1992) J Immunol 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PIPA epitope is an antibody that binds this PIPA epitope with greater affinity, avidity, more readily, and/or with greater duration than it binds to other PIPA epitopes or non-PIPA epitopes. It is also understood by reading this definition that, for example, an antibody (or moiety) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "immunologically active" in reference to an epitope being or "remaining immunologically active" refers to the ability of an antibody (e.g., anti-PIPA antibody) to bind to the epitope under different conditions, for example, after the epitope has been subjected to reducing or denaturing conditions.

As used herein, the terms "PIP", "antibody PIP" and "monoclonal antibody PIP" are used interchangeably to refer to immunoglobulin produced by a host cell with a deposit number of ATCC No. PTA-4220 or progeny thereof. The generation and characterization of PIP is described in Examples 1-3, below.

Different "biological functions" (or "properties") are associated with PIP, including, but not limited to, (a) ability to bind to PIPA; (b) ability to preferentially bind to the PIPA epitope to which PIP preferentially binds; (c) ability to bind PIPA on cancer cells, such as ovarian or colon cancer cells; (d) ability to bind to a portion of PIPA that is exposed on the surface of a living cell in vitro or in vivo; (e) ability to deliver a chemotherapeutic agent to cancerous cells (such as ovarian or breast cancer cells) expressing PIPA; and (f) ability to deliver a therapeutic agent or detectable marker into cancer cells expressing PIPA. As discussed herein, polypeptides (including antibodies) of the invention may have any one or more of these characteristics.

A "PIP equivalent antibody" or "PIP equivalent polypeptide" refers to an antibody or a polypeptide having one or more biological functions associated with PIP, such as, for example, binding specificity.

As used herein, "agent" refers to a biological, pharmaceutical, or chemical compound. Non-limiting examples include simple or complex organic or inorganic molecule, a peptide, a protein, an oligonucleotide, an antibody, an antibody derivative, or antibody fragment, a vitamin derivative, a carbohydrate, a toxin or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, an agent is said to be randomly selected when the agent is chosen randomly without considering the specific sequences involved in the association of PIPA with its native binding partners or known antibodies. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. This invention also encompasses agents that act at the sites of interaction between PIPA and its native binding partner, although other ligands and their active PIPA-interactive sites are also encompassed within the scope of this invention, whether currently known or later identified. Agents can be randomly selected or rationally designed by utilizing the peptide sequences that make up the contact sites of the receptor/ligand and/or PIPA/anti-PIPA antibody complex, for example, a rationally selected peptide agent can be a peptide whose amino acid sequence is identical to an epitope appearing on PIPA as it is exposed on the surface of a living cell in its native environment. Such an agent will reduce or block the association of the anti-PIPA antibody with PIPA, or the association of PIPA with its native ligand, as desired, by binding to the anti-PIPA antibody or to the native ligand.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because many of the polypeptides of this invention are based upon an antibody, the polypeptides can occur as single chains or associated chains.

Also encompassed within the scope of the invention are peptidomimetics of the PIPA peptide agonists, antagonists and modulators (including anti-PIPA antibodies) described herein. Such peptidomimetics include peptides wherein at least one amino acid reside is substituted with an amino acid reside that is not commonly found in nature, such as the D isomer of the amino acid or an N-alkylated species of the amino acid. In other embodiments, peptidomimetics are constructed by replacing at least one amide bond (—C(.dbd.O)—NH—) in a PIPA peptide agonist, antagonist or modulators with an amide isostere. Suitable amide isosteres include —CH.sub2.—NH—, —CH.sub2.—S—, —CH.sub2.—S(O).sub.n- (where n is 1 or 2), —CH.sub.2—CH.sub.2—, —CH.dbde.CH—(E or Z), —C(.dbd.O)—CH.sub.2—, —CH(CN)—NH—, —C(OH)—CH.sub.2—, and —O—C(.dbd.O)—NH—. The amide bonds in a PIPA agonist, antagonist or modulator that are suitable candidates for replacement with amide isosteres includes bonds that are hydrolyzable by the endogenous esterases or proteases of the intended subject of PIPA peptide agonist, antagonist or modulator treatment.

A "variable region" of an antibody refers to the variable region of the antibody light chain or the variable region of the antibody heavy chain, either alone or in combination.

A "constant region" of an antibody refers to the constant region of the antibody light chain or the constant region of the antibody heavy chain, either alone or in combination.

As used herein, "substantially pure" refers to material which is at least 50% pure (i.e., free from contaminants), at least 90% pure, at least 95% pure, at least 98% pure, or, preferably, at least 99%, or greater, pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention. An "effective amount" of a drug, compound, or pharmaceutical composition is an amount sufficient to effect beneficial or desired results including, without limitation, clinical results such as shrinking the size of the tumor (in the cancer context, for example, ovarian or colon cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) neoplastic or other diseased cells and to reduce and/or delay the development or growth of metastases of neoplastic cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. etc. from its original source.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) neoplastic or other diseased cells, reducing metastasis of neoplastic cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

The term "detection" as used herein includes qualitative and/or quantitative detection (measuring levels) with or without reference to a control.

As used herein, the term "labeled", with regard to the antibody, is intended to encompass direct labeling of the antibody by coupling (i.e., physically linking) a detectable substance, such as a radioactive agent or a fluorophore (e.g., fluorescein isothiocyanate (FITC) or phycoerythrin (PE)) to the antibody, as well as indirect laneling of the probe or antibody by reactivity with detectable substance.

As used herein, the term "association", with regard to the antibody, includes covalent and non-covalent attachment or binding to an agent (e.g., a toxin). The antibody can be associated with an agent (e.g., toxin) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such the agent's potency is not decreased.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, optionally a mammal, preferably a human. Mammals include, but are not limited to, farm animals, sport animals, pets, primates, mice and rats.

"Toxin" refers to any substance that effects an adverse response within a cell. For example, a toxin directed to a cancerous cell would have an adverse, sometimes deleterious effect, on the cancerous cell. Examples of toxins include, but are not limited to, radioisotopes, calicheamicin, and maytansinoids.

"Active immune response" refers to the development of, and on-going production of antibodies in vivo directed against an antigen, in response to the administration of the antigen, or the DNA coding for that antigen, to the host mammal by intravenous, intramuscular, subcutaneous, or other mode of administration with or without an adjuvant.

Methods of Making Antibodies and Polypeptides

This invention encompasses compositions, including pharmaceutical compositions, comprising anti-PIPA antibodies, polypeptides derived from anti-PIPA antibodies and polynucleotides comprising sequences encoding anti-PIPA antibodies and other agents as described herein. As used herein, compositions comprise one or more antibodies, polypeptides and/or proteins that bind to PIPA, PIPA agonists, antagonists, modulators, and/or one or more polynucleotides comprising sequences encoding one or more antibodies, polypeptides and proteins that bind to PIPA.

The invention further provides for conjugates of any PIPA peptide agonist, antagonist or modulator, and additional chemical structures that support the intended function or functions of the particular PIPA peptide agonist, antagonist or modulator, these conjugates include PIPA peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (eds) Affinity Chromatography: A Practical Approach, IRL Press (1985); Lowe, "An Introduction to Affinity Chromatography", in work et al. (eds) Laboratory Techniques in Biochemistry and Molecular Biology, Vol. 7, Part II, North-Holland (1979); Porath et al., "Biospecific Affinity Chromatography", in Neurath et al. (eds), The Proteins, 3rd ed., Vol. 1, pp. 95-178 (1975); and Schott, Affinity Chromatography, Dekker (1984).

Also provided herein are conjugates of PIPA peptide agonist, antagonist or modulator and any reporter moiety used in the diagnostic procedures discussed herein.

The PIPA peptide agonist, antagonist or modulator agents, polypeptides and proteins of this invention, including PIP or PIP-equivalent antibodies, are further identified and characterized by any (one or more) of the following criteria: (a) ability to bind to PIPA (including PIPA on cancer cells, including but not limited to ovarian, prostate, pancreatic, lung, colon, uterine, or breast cancer cells); (b) ability to preferentially bind to the PIPA epitope to which PIP preferentially binds; and (c) ability to bind to a portion of PIPA that is exposed on the surface of a living cell in vitro or in vivo; (d) ability to bind to a portion of PIPA that is exposed on the surface of living cancer cells, such as but not limited to ovarian, prostate, pancreatic, lung, colon, uterine, or breast cancer cells; (e) ability to deliver a chemotherapeutic agent or detectable marker to cancerous cells (such as but not limited to ovarian, prostate, pancreatic, lung, colon, uterine, or breast cancer cells) expressing PIPA; (f) ability to deliver a toxin to cancerous cells (such as but not limited to ovarian and colon cancer cells) expressing PIPA; (g) ability to deliver a therapeutic agent into cancerous cells (such as but not limited to ovarian and colon cancer cells) expressing PIPA.

In some embodiments, the antibody of the invention is an antibody PIP that is produced by a host cell with a deposit number of ATCC No. PTA-4220, or progeny thereof. The present invention also encompasses various formulations of PIP and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of PIP that comprises an antigen (PIPA), recognition site of the required specificity. The invention also provides human antibodies displaying one or more of the biological characteristics of PIP. The equivalent antibodies of PIP (including chimerized or humanized antibodies and human antibodies), polypeptide fragments of PIP, and polypeptides comprising any of these fragments are identified and characterized by any (one or more) of the seven criteria described above.

In some embodiments, the antibodies, polypeptides and proteins of the invention that bind to PIPA are antibodies, polypeptides and proteins that competitively inhibit preferential binding of a herein-specified anti-PIPA antibody, PIP. In some embodiments, the antibodies, the polypeptides and the proteins preferentially bind to the same epitope on PIPA as the antibody mu-PIP preferentially binds.

Accordingly, the invention provides any of the following (or compositions, including pharmaceutical compositions, comprising any of the following): (a) antibody PIP produced by the host cell with a deposit number of ATCC No. PTA-4220 or its progeny; (b) a humanized form of antibody PIP; (c) an antibody comprising one or more of the light chain and/or heavy chain variable regions of antibody PIP; (d) a chimeric antibody comprising variable regions homologous or derived from variable regions of a heavy chain and a light chain of antibody PIP, and constant regions homologous or derived from constant regions of a heavy chain and a light chain of a human antibody; (e) an antibody comprising one or more of the light chain and/or heavy chain CDRs (at least one, two, three, four, five, or six) of PIP; (f) an antibody comprising a heavy and/or a light chain of PIP; (g) a human antibody that is equivalent to PIP. A humanized form of the antibody may or may not have CDRs identical to PIP, or antibody produced by the host cell with a deposit number of ATCC No. PTA-4220, or the progeny thereof. Determination of CDR regions is well within the skill of the art. In some embodiments, the invention provides an antibody that comprises at least one CDR that is substantially homologous to at least one CDR of PIP, or derived from PIP, or antibody produced by the host cell with a deposit number of ATCC No. PTA-4220. Other embodiments include antibodies which have at least two, three, four, five, or six CDR(s) that are substantially homologous to at least two, three, four, five or six CDRs of PIP or derived from PIP, or antibody produced by the host cell with a deposit number of ATCC No. PTA-4220. It is understood that, for purposes of this invention, binding specificity and/or overall activity (which may be in terms of reducing the growth and/or proliferation of cancerous cells, inducing apoptotic cell death in the cancer cell, delaying the development of metastasis, and/or treating palliatively) is generally retained, although the extent of activity may vary compared to PIP (may be greater or lesser). The invention also provides methods of making any of these antibodies. Methods of making antibodies are known in the art and are described herein.

The invention also provides polypeptides comprising an amino acid sequence of the antibodies of the invention, such as PIP. In some embodiments, the polypeptide comprises one or more of the light chain and/or heavy chain variable regions of the antibody PIP. In some embodiments, the polypeptide comprises one or more of the light chain and/or heavy chain CDRs of PIP. In some embodiments, the polypeptide comprises three CDRs of the light chain and/or heavy chain of PIP. In some embodiments, the polypeptide comprises an amino acid sequence of PIP that has any of the following: at least 5 contiguous amino acids of a sequence of PIP, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of PIP. In one embodiment, the variable region is from a light chain of PIP. In another embodiment, the variable region is from a heavy chain of PIP. In another embodiment, the 5 (or more) contiguous amino acids are from a complementarity-determining region (CDR) of PIP.

In some embodiments of this invention, cells of this invention that express PIPA, portion of PIPA, PIP or PIP-equivalent antibodies, or other PIPA-binding polypeptides of this invention are administered directly to an individual to modulate their in vivo PIPA biological activity.

Antibodies may be polyclonal (e.g., not homogeneous) or monoclonal. Methods of making monoclonal antibodies are known in the art. One method which may be employed is the method of Kohler and Milstein, Nature 256:495-497 (1975) or a modification thereof. In general, a mouse or rat is used for immunization but other animals may also be used. The immunogen can be, but is not limited to, primary cells, cultured cell lines, cancerous cells, nucleic acids, or tissue. In one embodiment, human Mullerian duct-derived epithelial cells are used. Methods for isolating and culturing Mullerian duct-derived epithelial cells (see U.S. Pat. No. 6,416,999) are detailed in Example 1, below. Cells used for immunogen, for example, Mullerian duct-derived epithelial cells, may be cultured for a period of time (at least 24 hours) prior to their use as an immunogen. Cells (e.g., Mullerian duct-derived epithelial cells) may be used as immunogens by themselves or in combination with a non-denaturing adjuvant, such as Ribi. In general, cells (e.g., Mullerian duct-derived epithelial cells) should be kept intact and preferably viable when used as immunogens. Intact cells may allow antigens to be detected better than ruptured cells. Use of denaturing or harsh adjuvants, e.g., Freud's adjuvant, may rupture the Mullerian duct-derived epithelial cells and therefore is discouraged. In another embodiment, full length PIPA or any fragments of PIPA, or PIPA expressing cancer cells are used as immunogens. The immunogen may be administered multiple times at periodic intervals such as, bi-weekly, or weekly, or may be administered in such a way as to maintain viability in the animal (e.g., in a tissue recombinant).

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen (e.g., surface of Mullerian duct-derived epithelial cells, surface of cancer cell lines, PIPA, etc.) using FACS or immunohistochemistry (IHC) screening. The selected monoclonal antibody-secreting hybridomas are then cultured either in vitro (e.g., in tissue culture bottles or hollow fiber reactors), or in vivo (e.g., as ascites in mice). Examples 2-3, below, further detail the methods utilized to obtain and screen an antibody PIP which bind to PIPA. Methods of culturing hybridoma under conditions to generate the antibody PIP, and purifying the antibody are known in the art and are also further detailed in Examples 2 and 3.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, the monoclonal antibody PIP and any other equivalent antibodies can be sequenced and produced recombinantly by any means known in the art (e.g., humanization, use of transgenic mice to produce fully human antibodies, phage display echnology, etc.). In one embodiment, PIP monoclonal antibody is sequenced and the polynucleotide sequence is then cloned into a vector for expression or propagation. The sequence encoding the antibody of interest may be maintained in a vector in a host cell. The host cell can then be expanded and frozen for future use.

FIG. 4 shows the nucleic acid and corresponding translated protein sequence of the variable region of the kappa light chain of the PIP monoclonal antibody, including the native signal sequence. Also included in FIG. 4 is the nucleic acid and corresponding translated protein sequence of the variable region of the heavy chain of the PIP onoclonal antibody, including the native signal sequence.

Monoclonal antibody-secreting hybridomas described above can be selected for producing antibodies that bind preferentially to the epitope on PIPA that the antibody PIP preferentially binds. Methods of selecting such antibody are known in the art. For example, binding competition assays can be used to determine whether an antibody binds to the same epitope as PIP. An antibody's competition with PIP for binding to PIPA indicates that the antibody binds preferentially to the epitope that PIP binds. Binding competition assays are well known in the art. Polypeptides that bind preferentially to the epitope on PIPA that the antibody PIP binds preferentially can also be tested and identified using similar methods.

In another alternative, the antibody PIP or any other antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using PIPA for cells expressing the antibody or protein of interest. The "panning" procedure is conducted-by obtaining a cDNA library from tissues or cells that express the antibody or protein of interest, over-expressing the cDNAs in a second cell type, and screening the transfected cells of the second cell type for a specific binding to PIPA. Detailed descriptions of the methods used in cloning mammalian genes coding for cell surface proteins by "panning" can be found in the art. See, for example, Aruffo, A. and Seed, B. *Proc. Natl. Acad. Sci. USA*, 84, 8573-8577 (1987) and Stephan, J. et al., *Endocrinology* 140: 5841-5854 (1999).

cDNAs can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include, but are not limited to, plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cell, include but are not limited to, COS, HeLa, and CHO cells. Preferably, the host cells express the cDNAs at a level of about 5 fold higher, about 10 fold higher, or, preferably, about 20 fold higher than that of the corresponding endogenous antibody or protein of interest, if present, in the host cells. Screening the host cells for a specific binding to PIPA is effected by an immunoassay or FACS. A cell overexpressing the antibody or protein of interest can be identified.

The invention includes polypeptides comprising an amino acid sequence of the antibodies of this invention, such as PIP. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, a PIP polypeptide could be produced by an automated polypeptide synthesizer employing the solid phase method.

The invention also encompasses single chain variable region fragments ("scFv") of antibodies of this invention, such as PIP. Single chain variable region fragments are made by linking light and/or heavy chain variable regions by using a short linking peptide. Bird et al. (1988) *Science* 242: 423-426. An example of a linking peptide is (GGGGS)$_3$ (SEQ ID NO:1), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to antibodies, such as antibody PIP, including functionally equivalent antibodies and polypeptides of PIP, which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified PIP polypeptides are made using established procedures in the art and can be screened using standard assays known in the art, some of which are described below and in Example 3, below.

The invention also encompasses fusion proteins comprising one or more fragments or regions from the antibodies of this invention, such as PIP. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of PIP. For purposes of this invention, a PIP fusion protein contains one or more PIP polypeptides and another amino acid sequence to which it is not attached in the native molecule, for example, a heterologous sequence or a homologous sequence from another region. A PIP polypeptide can be created by methods known in the art, for example, synthetically or recombinantly.

In another embodiment, PIP chimeras are provided in which the heavy and/or light chains are fusion proteins. In some embodiments, the constant domain of the chains is from one particular species and/or class, and the variable domains are from a different species and/or class. For instance, a chimeric antibody (in some embodiments) is one in which the constant regions are derived from human origin, and the variable regions are homologous or derived from PIP (i.e., murine). Also embodied within the invention is an antibody with a humanized variable region, in which (in some embodiments) the CDR regions comprise PIP amino acid sequences, while the framework regions are derived from human sequences. Other forms of humanized antibodies are known in the art and described herein. Also embodied are functional fragments of chimeras. An example is a humanized Fab fragment, which contains a human hinge region, a human first constant region, a human kappa light or heavy chain constant region, and the variable region of light and/or heavy chain from PIP. The humanized PIP Fab fragments can in turn be made to form Fab dimers. Typically, the PIP fusion proteins and PIP chimeras of this invention are made by preparing an expressing a polynucleotide encoding them using recombinant methods described herein, although they may also be prepared by other means known in the art, including, for example, chemical synthesis. See, for example, U.S. Pat. Nos. 5,807,715; 4,816,567; and 6,331,415.

The invention also encompasses humanized antibodies. The polynucleotide sequence of an antibody, such as PIP or an equivalent antibody, may be used for genetic manipulation to generate a "humanized" antibody, or to improve the affinity, or other characteristics of the antibody. The general principle in humanizing an antibody involves keeping the antigen-binding portion of the antibody unchanged while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, ie., deciding which antibody framework region to use during the humanizing process (3) the actual humanizing methodologies/techniques and (4) the transfection and expression of the humanized antibody. For example, the constant region may be engineered to more resemble human constant regions to avoid immune response if the antibody is used in clinical trials and treatments in humans. See, for example, U.S. Pat. Nos. 5,997,867 and 5,866,692.

A number of "humanized" antibody molecules comprising an antigen-binding site derived from a non-human immunoglobulin have been described, including chimeric antibodies having rodent V regions and their associated complementarity determining regions (CDRs) fused to human constant domains. See, for example, Winter et al. *Nature* 349:293-299 (1991); Lobuglio et al. *Proc. Nat. Acad. Sci. USA* 86:4220-4224 (1989); Shaw et al. *J Immunol*. 138:4534-4538 (1987); and Brown et al. *Cancer Res*. 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988); Verhoeyen et al. *Science* 239:1534-1536 (1988); and Jones et al. *Nature* 321:522-525 (1986). Another reference describes rodent CDRs supported by recombinantly veneered rodent FRs. See, for example, European Patent Publication No. 519,596. These "humanized" molecules are designed to minimize unwanted immunological response toward rodent antihuman antibody molecules that limit the duration and effectiveness of therapeutic applications of those moieties in human recipients. Other methods of humanizing antibodies that may also be utilized are disclosed by Daugherty et al., *Nucl. Acids Res.*, 19:2471-2476 (1991) and in U.S. Pat. Nos. 6,180,377; 6,054,297; 5,997,867; and 5,866,692.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Monoclonal antibodies to PIPA may be used for therapeutic purposes in individuals with cancer or other diseases. Therapy with PIP or PIP equivalent antibodies can involve formation of complexes both in vitro and in vivo as described above. In one embodiment, monoclonal antibody PIP can bind to and reduce the proliferation of cancerous cells. It is understood that the antibody is administered at a concentration that promotes binding at physiological (e.g., in vivo) conditions. In another embodiment, monoclonal antibody PIP can be used for immunotherapy directed at cancerous cells of different tissues such as but not limited to ovary, colon, lung, breast, uterus, prostate, pancreas, kidney and other types of cancer such as sarcoma. In another embodiment, monoclonal antibody PIP alone can bind to and reduce cell division in the cancer cell. In another embodiment, monoclonal antibody PIP can bind to cancerous cells and delay the development of metastasis. In yet another embodiment, an individual with cancer is given palliative treatment with PIP. Palliative treatment of a cancer individual involves treating or lessening the adverse symptoms of the disease, or iatrogenic symptoms resulting from other treatments giving for the disease without directly affecting the cancer progression. This includes treatments for easing pain, nutritional support, sexual problems, psychological distress, fatigue, psychiatric disorders, nausea, vomiting, etc.

In such situations, PIP may be administered with agents that enhance or direct an individual's own immune response, such as an agent that strengthens ADCC.

In yet another embodiment, monoclonal antibody PIP could be conjugated to or associated with a radioactive molecule, toxin (e.g., calicheamicin), chemotherapeutic molecule, liposome or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, PIP is internalized by the cell bearing PIPA at its surface, thus delivering the conjugated moiety to the cell to induce the therapeutic effect. In yet another embodiment, the antibody can be employed as adjuvant therapy at the time of the surgical removal of a cancer expressing the antigen in order to delay the development of metastasis. The antibody can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

Cell cycle dosing is contemplated in the practice of this invention. In such embodiments, a chemotherapeutic agent is used to synchronize the cell cycle of the tumor or other target diseased cells at a pre-determined stage. Subsequently, administration of PIP (alone or with an additional therapeutic moiety) is made. In alternative embodiments, PIP is used to synchronize the cell cycle and reduce cell division prior to administration of a second round of treatment; the second round may be administration of PIP or a PIP-equivalent antibody and/or an additional therapeutic moiety.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli L-asparaginase*, emetine, epoetin alfa, Erwinia *L-asparaginase*, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon alfa-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

A radioactive molecule of this invention includes any radioisotope that is effective in destroying a cancerous cell. Examples include, but not limited to, cobalt-60 and X-rays. Additionally, naturally occurring radioactive elements such as uranium, radium, and thorium which typically represent mixtures of radioisotopes, are suitable examples of a radioactive molecule.

The antibodies of the invention can be internalized within the diseased or carcinoma cells to which they bind and are therefore particularly useful for therapeutic applications, for example, delivering into the cells toxins needed to be internalized for their adverse activity. A toxin of the invention include, but not limited to, taxol, cytochalasin B, gramicidin D, ethidium bromide, emetine, mitomycin, etoposide, tenoposide, vincristine, vinblastine, colchicin, doxorubicin, daunirubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In a preferred embodiment, the cytotoxin is especially effective in dividing or rapidly dividing cells, such that non-dividing cells are relatively spared from the toxic effects.

The antibodies or polypeptides of the invention can be conjugated (linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the therapeutic molecule at any location along the antibody so long as the antibody is able to bind its target PIPA.

A toxin or a therapeutic agent may be coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and therapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or suulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a therapeutic agent via a microcarrier. Microcarrier refers to a biodegradable or a non-biodegradable particle which is insoluble in water and which has a size of less than about 150, 120 or 100 µm in size, more commonly less than about 50-60 µm, preferably less than about 10, 5, 2.5, 2 or 1.5 µm. Microcarriers include "nanocarriers", which are microcarriers having a size of less than about 1 µm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5] undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saporin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or therapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al., *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal Antibodies", D. M. Goldenberg ed. (CRC Press, Boca Raton, 1995).

Alternatively, an antibody can be conjugated to a second antibody to form an antibody heteroconjugate as described by Segal in U.S. Pat. No. 4,676,980. the formation of cross-linked antibodies can target the immune system to specific types of cells, for example, cancer or diseased cells expressing PIPA.

An antibody (or polypeptide) of this invention may be linked to a labeling agent (alternatively termed "label") such as a fluorescent molecule, a radioactive molecule or any others labels known in the art. Labels are known in the art that generally provide (either directly or indirectly) a signal.

The ability of the antibodies, polypeptides and proteins of this invention, such as ability to inhibit growth of cancerous cells expressing PIPA, ability to delay development of metastasis in an individual with cancer expressing PIPA ability to deliver a therapeutic agent, such as a toxin, or a radioactive compound, to cancerous cells expressing PIPA, may be tested using methods known in the art.

The invention also provides compositions (including pharmaceutical compositions) comprising antibody PIP or PIP equivalent antibodies (which, as this disclosure makes clear, include all of the antibodies described herein) or polypeptides and a therapeutic agent.

In yet another embodiment, any of the PIPA binding embodiments described herein can bind to PIPA-expressing cancerous cells and induces an active immune response against the cancerous cells expressing PIPA. In some cases, the active immune response can cause death of the cancerous cells (e.g., antibody binding to cancer cells inducing apoptotic cell death), or inhibit the growth (e.g., block cell cycle progression) of the cancerous cells.

Methods for Screening Monoclonal Antibodies

Several methods may be used to screen monoclonal antibodies that bind to PIPA. It is understood that "binding" refers to biologically or immunologically relevant binding, i.e., binding which is specific for the unique antigen for which the immunoglobulin molecule is encoded, or to which the polypeptide is directed. It does not refer to non-specific binding that may occur when an immunoglobulin is used at a very high concentration against a non-specific target. In one embodiment, monoclonal antibodies are screened for binding to PIPA using standard screening techniques. In this manner, PIP monoclonal antibody was obtained. In accordance with the Budapest Treaty, a hybridoma which produces PIPA monoclonal antibodies (1hFT.1.6D4.1C8) has been deposited in the American Type Culture Collection (ATCC) 10801 University Blvd., Manassas Va. 20110-2209 on Apr. 9, 2002 with a Patent Deposit Designation of PTA-4220.

Monoclonal antibodies that bind to PIPA are screened for binding to cancerous cells and tissues and non-cancerous cells and tissues. In one embodiment, monoclonal antibodies which bind to PIPA and that are also cross reactive to human cancerous cells or tissues, but not to normal cells or tissues to the same degree, are selected. One method that may be employed for screening is immunohistochemistry (IHC). Standard immunohistochemical techniques are known to those of average skill in the art. See, for example, *Animal Cell Culture Methods* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if PIPA is present only on cancerous cells, PIP may be used to detect the presence of PIPA on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining. Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include but are not limited to carcinomas, adenocarcinomas, sarcomas, adenosarcomas, lymphomas, and leukemias.

In yet another alternative, cancerous cells lines such as SK-Ov-3 (ATCC No. HTB 77), OVCAR-3 (ATCC No. HTB 161), LnCaP (ATCC No. CRL-1740), COLO 205, (ATCC No. CCL 222), A549 (ATCC No. CCL 185), PANC-1 (ATCC No. CRL 1469), SK-BR-3 (ATCC No. HTB 30), SK-MES-1 (ATCC No. HTB 58), HT-29 (ATCC No. HTB-38), H9 (ATCC No. HTB-176), SW 480 (ATCC No. CCL 228), AsPC-1 (ATCC No. CRL 1682), Capan-1 (ATCC No. HTB-79), CFPAC-1 (ATCC No. CRL 1918), HPAF-II (ATCC No. CRL-1997), HS 700T (ATCC No. HTB 147), ES-2 (ATCC No. CRL-1978), OV-90 (ATCC No. CRL-11732) and PC-3 (ATCC No. CRL 1435) and normal cells from their respective tissues may be used to screen for monoclonal antibodies which are specific for cancerous tissue. Primary, or low passage, cell cultures derived from normal tissues from different organs, including but not limited to, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in U.S. Pat. No. 6,406,840, and screened for the binding of antibody using IHC as described above for tissues. Alternatively, cells may be removed from the growth surface using non-proteolytic means and spun into a pellet which is then embedded and treated as tissues for IHC analysis as described above. In another alternative, single cells may be screened by incubating with the primary antibody, a secondary "reporter" antibody linked to a fluorescent molecule and then analyzed using a fluorescent activated cell-sorting (FACS) machine.

Several different detection systems may be utilized to detect binding of antibodies to tissue section. Typically, immunohistochemistry involves the binding of a primary antibody to the tissue and then a secondary antibody reactive against the primary antibody is generated and conjugated to a detectable marker (e.g., horseradish peroxidase, HRP, or biotin). One alternative method that may be used is polyclonal mirror image complementary antibodies or polyMICA. PolyMICA (polyclonal Mirror Image Complementary Antibodies) technique, described by D. C. Mangham and P.G. Isaacson (*Histopathology* (1999) 35(2):129-33), can be used to test binding of primary antibodies (e.g., PIP) to normal and cancerous tissue. Several kinds of polyMICA™ Detection kits are commercially available from The Binding Site Limited (P.O. Box 4073 Birmingham B29 6AT England). Product No. HK004.D is a polyMICA™ Detection kit which uses DAB chromagen. Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies PIPA(e.g., PIP) made by hybridomas created from mice immunized with an immunogen (e.g., Mullerian duct-derived epithelial cell) recognizing one antigen (e.g., PIPA) to various tissues or cells. In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

Epitope mapping may be used to further characterize the antibody. Commercially available services (e.g., Pepscan Systems, P.O. Box 2098, 8203 AB Lelystad, The Netherlands) may be used to determine the epitope(s) on the antigen to which an antibody, such as PIP, binds.

Methods of Identifying and Characterizing PIPA

Several methods may be employed to identify an antigen of interest. One method is to utilize antibodies for affinity purification. Cell lysates/extracts or tissue homogenates/extracts may be applied to an affinity resin in which the antibody has been attached to a solid support. The samples to be extracted can be obtained from any number of sources, including but not limited to normal or cancerous tissues, biological samples from individuals with a cancer or another disease state, commercial sources (e.g., ATCC), or a cell line. The antibodies that are used for affinity purification may be obtained in various manners that are discussed in detail below. Once the antigen has been bound to the support, the antigen can be eluted using different reagents. These reagents include but are not limited to low pH reagents and chemical denaturants (e.g., urea or guanidine HCl). See, for example, Current Protocols in Immunology (J. E. Coligan et al., eds., Volume 2, 1991, 8.2.1-8.2.9).

The purified antigen may be used for sequencing using standard sequencing methods known in the art (e.g., Edman degradation). If peptide sequences are obtained, then degenerate primers or probes can be made from the peptide sequences. The probes can then be hybridized to cDNA libraries in order to identify those bacteria containing inserts that contain the DNA encoding the protein under study. See, for example, Sambrook et al. or Ausubel et al. above.

Another method that can be used for identifying and characterizing an antigen is to use Western-blotting techniques. PIPA was identified in one aspect by Western blotting with cell lysates from various human cancers and monoclonal antibody PIP. As noted above, the hybridoma (1hFT.1.6D4.1C8) producing this antibody was deposited at the American Type Culture Collection (ATCC) 10801 University Blvd., Manassas, Va. 20110-2209, on Apr. 9, 2002 (PTA-4220). As is known to one of skill in the art, Western blotting can involve running cell lysates and/or cell fractions on a denaturing or non-denaturing gel, transferring the proteins to nitrocellulose paper, and then probing the blot with an antibody (e.g., PIP) to see which proteins are bound by the antibody. This procedure is detailed further in Examples 7 and 8, below.

Another method that can be used to characterize antigens to which PIP bind is mass spectrometry analysis. Several types of mass spectrometry analysis may be performed. In one approach, the masses of a tryptic digest of the protein are measured by matrix assisted laser desorption/ionization (MALDI) time-of-flight mass spectrometry (MALDI-TOF-MS) and the resulting list of peptide masses are used as a "fingerprint" of the protein in sequence database searches. In matrix assisted laser desorption/ionization (MALDI), the peptides are co-crystallized with a large excess of a light-absorbing matrix. Irradiation of the crystals by a pulsed laser beam results in the rapid sublimation of matrix and the embedded peptide molecules and the generation of intact gas phase ions. For peptides, protonated, singly charged molecular ions are usually formed. The mass/charge ratio (m/z) is measured at high mass accuracy time-of-flight analysis, optionally employing delayed-extraction and/or a reflectron. The retrieved sequences are evaluated by mass accuracy of the peptides, matching of additional peptide masses in the MALDI spectrum after accounting for common modifications such as oxidation, acrylamidation of cysteine and missed cleavages and the use of secondary information (apparent isoelectric point and molecular weight). If any ambiguity about the identification by MALDI-TOF-MS still exists, the results can be verified by mass spectrometric peptide sequencing. These and other procedures for using mass spectroscopy to identify known proteins are reviewed in *Use of Mass Spectrometry to Study Signaling Pathways* (A. Pandey, J. S. Andersen, and M. Mann; 2000).

The antigen PIPA recognized by a monoclonal antibody of the present invention is first isolated by any method described above and alternatively, can be isolated by any methods known to the average skilled artisan. The protein band which is bound by the antibody can be characterized by first digesting the purified protein with a protease, which results in a mixture of peptides. The peptides are then analyzed by MALDI mass spectroscopy.

Another mass spectroscopy method that may be used is nanoelectrospray tandem mass spectrometry. In this method, a solution of peptide molecules is passed through a needle maintained at a high potential. At the end of the needle, the solution is dispersed into a fine mist of small, highly charged droplets containing peptide molecules. These small droplets evaporate rapidly resulting in the release of multiple charged molecular ions into the gas phase. Once the peptides are in the gas phase, they are transported through an orifice into a mass spectrometer where they are separated and detected according to their mass to charge (m/z) ratio. Nanoelectrospray refers to a refined version of electrospray where an extremely fine needle disperses the sample at flow rates in the nanoliter per minute range. This greatly reduces the droplet diameter and enhances the sensitivity of detection of peptides. Electrospray tends to be more sensitive to the presence of salts than MALDI-TOF-MS. Therefore, the samples are first desalted by methods known to skilled artisans. The electrospray ion source is compatible with mass spectrometers that allow peptide sequencing (the most common are triple quadrupole, ion trap, or quadrupole-time-of-flight mass spectrometers). In low-level protein identifications, the peptide signals are often obscured by the chemical background or signals from contaminants. High-resolution instruments (e.g., a quadrupole-time-of-flight instrument) help to resolve peptides from the chemical background. Alternatively, in a triple quadrupole instrument, a precursor-ion scan enables selective detection of peptides in the presence of non-peptide contaminants.

In another alternative, the antigen or protein of interest may be subjected to sequencing by Edman degradation, which is well known to those of skill in the art. The peptide information generated from mass spectrometry or Edman degradation can be used to design probes or primers that are used to clone the antigen of interest.

An alternative method of cloning a target antigen that is a cell surface antigen is by "panning" the antibodies for cells expressing the cell surface antigen of interest. The "panning" procedure is conducted by obtaining the cDNAs of cells that express the antigen of interest, over-expressing the cDNAs in a second cell type, and screening cells of the second cell type for a specific binding to the monoclonal antibody. Detailed descriptions of the methods used in cloning mammalian genes coding for cell surface proteins by "panning" can be found in the art. See, for example, Aruffo, A. and Seed, B.

Proc. Natl. Acad. Sci. USA, 84, 8573-8577 (1987) and Stephan, J. et al., *Endocrinology* 140: 5841-5854 (1999).

cDNAs can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antigens in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the target antigens. Non-limiting examples of mammalian host cells include but are not limited to COS, HeLa, and CHO cells. Preferably, the host cells express the cDNAs at a level of about 5 fold higher, about 10 fold higher, or, preferably, about 20 fold higher than that of the corresponding endogenous antigens, if present, in the host cells. Screening the host cells for a specific binding to the selected monoclonal antibodies is effected by an immunoassay or fluorescent activated cell sorting (FACS). By identifying the individual target antigens, the combination of antigens expressed in a specific cell type can then be determined.

PIPA can be further characterized by its location within a cell. Without being bound by theory, in some tumor tissues and tumor-derived cell lines, PIPA is a cell-associated antigen that is expressed at least on the surface of a cell. Since the method of generating monoclonal antibody PIP involved using intact cells as immunogen, the monoclonal antibody that was generated was most likely against an antigenic determinant on the surface of the cell. Such cell surface proteins may, however, also be present inside the cell in addition to the cell surface, secreted from the cell or released from the cell surface. Additionally, these cell surface proteins may be present on surface or interior of different cells, secreted by cells, or at different stages of the cell cycle.

Further characterization of antigen can be accomplished by determining expression patterns on different tissues or cells, copy number on cells and/or tissues, and by the antibodies that bind to it. In one aspect, the expression patterns may be determined by using immunohistochemical techniques with biological samples. The expression pattern of the antigen can be assessed in individuals with and without cancer or alternatively another disease state. Copy number of antigens can be determined by using standard Scatchard analysis.

Methods of Using PIPA

Once an antigen (e.g., PIPA) has been identified and characterized, the information about the antigen (e.g., sequence) may be used for various purposes. In one aspect, the sequence of PIPA may be used to make antibodies that bind to it. For example, PIPA sequence can be cloned into an expression vector and expressed in a suitable host cell to make an immunogen for animal injections and subsequent generation of hybridomas. Methods of making antibodies are described below. In another aspect, PIPA sequence may be used to make an antibody recombinantly. Methods of making recombinant antibodies are well known in the art. See, for example, *Current Protocols in Immunology* (J. E. Coligan et al., eds., 1991) and U.S. Pat. Nos. 5,665,570; 5,677,425; 5,760,185; 5,773,247; and 5,929,212.

Another use for PIPA is for drug screening purposes as a possible receptor for a protein or small molecule ligand. Drugs, compounds, proteins, small molecules, and pharmaceutical compositions can be tested for their ability to bind to PIPA and any effects resulting from such binding. PIPA may be bound to a substrate and monitored for effects. Such effects may include but are not limited to changes in intracellular pathway regulation, apoptosis, cellular activation, cellular metabolism, or cellular anergy. Binding of PIPA may elucidate its biological role (e.g., regulatory protein, protein associated with growth, differentiation, or development, etc.).

Another use for PIPA is for purification of antibodies against PIPA. In one embodiment, mammals may be immunized with any immunogen, (e.g., cancerous cells) and their splenocytes can be removed and used to make hybridomas. The hybridoma supernatants may be passed over an affinity column in which PIPA is immobilized.

PIPA as a protein, or as nucleic acid contained in a vector which expresses the protein in human tissue, may be used for vaccination purposes (e.g., active). In some cases, PIPA can be administered for vaccination with an adjuvant. In other cases, an adjuvant is not used and PIPA is administered neat. While the routes of administration are varied for vaccinations, standard routes of vaccination are injection and oral ingestion. See, for example, U.S. Pat. Nos. 6,221,644; 6,117,653; 6,110,724; and 5,932,225.

Yet another use for PIPA is to use PIPA or portions thereof for high-throughput screening. For example, PIPA DNA sequences may be immobilized to solid or semi-solid substrate, and DNA isolated from biological samples from a panel of individuals can be used to determine if hybridization occurs. In one embodiment, complimentary strands of nucleic acids are used to optimize hybridization. This approach can be useful for screening individuals for cancerous, or other, cells that express PIPA.

Methods of Diagnosing Cancer Using PIP, PIP-equivalent Antibodies or PIP-equivalent Polypeptides that Bind to PIPA.

Monoclonal antibody PIP and equivalent antibodies or polypeptides made by the methods disclosed herein may be used to identify the presence or absence of cancerous cells in a variety of tissues, including but not limited to, ovary, breast, lung, prostate, colon, kidney, skin, thyroid, brain, heart, liver, stomach, nerve, blood vessels, bone, and upper digestive tract for purposes of diagnosis. Monoclonal antibodies to PIPA made by the methods disclosed herein may also be used to identify the presence or absence of cancerous cells, or the level thereof, which are circulating in blood after their release from a solid tumor. Such circulating antigen may be an intact PIPA antigen, or a fragment thereof that retains the ability to be detected to the methods taught herein. Such detection may be effected by FACS analysis using standard methods commonly used in the art.

These uses can involve the formation of a complex between PIPA and an antibody that binds specifically to PIPA. Examples, of such antibodies include but are not limited to those PIPA monoclonal antibodies produced by the hybridoma deposited in the ATCC with the designation PTA-4220. The formation of such a complex can be in vitro or in vivo. Without being bound by theory, monoclonal antibody PIP can bind PIPA through the extracellular domain of PIPA and may then be internalized.

In a preferred embodiment of the diagnostic methods of this invention, the antibody bears a detectable label. Examples of labels that may be used include a radioactive agent or a fluorophore, such as fluoroisothiocyanate (FITC) or phycoerythrin. As with other known antibodies used commercially for diagnostic and therapeutic purposes, the target antigen of this invention PIPA, has limited expression in normal tissue. It is up regulated in some tumors. In particular, it is up regulated in a variety of ovarian tumors. Therefore, the particular dosages and routes of delivery of the antibodies of this invention as used for diagnostic or therapeutic agents will be tailored to the particular tumor or disease state at hand, as well as to the particular individual being treated.

One method of using the antibodies or polypeptides for diagnosis if the antigen is a cell surface antigen is in vivo tumor imaging. In vivo tumor imaging involves linking the antibody or polypeptide to a radioactive or radioopaque agent, administering the antibody or polypeptide to the patient and using an x-ray or other imaging machine to visualize the localization of the labeled antibody or polypeptide at the surface of cancer cells expressing the antigen. The antibody is administered at a concentration that promotes binding at physiological conditions.

In vitro techniques for detection of PIPA are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumors or neoplasms, or of measuring the effectiveness of a method of treatment with a radiolabelled antibody, comprising the step of administering a radiolabelled, tumor-specific antibody to an individual following the practice of this invention. The radiolabelled antibody may be a monoclonal or polyclonal antibody comprising a radiolabel, preferably selected from the group consisting of Technetium-99 m, Indium-111, Iodine-131, Rhenium-186, Rhenium-188, Samarium-153, Lutetium-177, Copper-64, Scandium-47, Yttrium-90. Monoclonal antibodies labelled with therapeutic radionuclides such as Iodine-131, Rhenium-188, Holmium-166, Samarium-153, and Scandium-47, which do not compromise the immunoreactivity of antibodies and are not broken down in vivo, are especially preferred. The person skilled in the art will appreciate that other radioactive isotopes are know, and may be suitable for specific applications, the radio-imaging may be conducted using Single Photon Emission Computer Tomography (SPECT), Position Emission Tomography (PET), Computer Tomography (CT) or Magnetic Resonance Imagining (MRI). Correlative imaging, which permits greater anatomical definition of location of metastases located by radioimmunoimaging, is also contemplated.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify neoplasms at different stages of development. The antibodies may also be used to determine which individuals' tumors express the antigen on their surface at a pre-determined level and are thus candidates for immunotherapy using antibodies directed against said antigen, the antibodies may recognize both primary and metastasizing cancers of the ovary, prostate, colon, uterus, and other cancers that express PIPA. As used herein, detection may include qualitative and/or quantitative detection and may include comparing the level measured to a normal cell for an increased level of expression of PIPA in cancerous cells.

The invention also provides methods of aiding diagnosis of cancer (such as ovarian, lung, pancreatic, prostate, colon, uterine, or breast cancer) in an individual using any antibody that binds to PIPA and any other methods that can be used to determine the level of PIPA expression. As used herein, methods for "aiding diagnosis" means that these methods assist in making a clinical determination regarding the classification, or nature, of cancer, and may or may not be conclusive with respect to the definitive diagnosis. Accordingly, a method of diagnosis of cancer can comprise the step of detecting the level of PIPA in a biological sample from the individual and/or determining the level of PIPA expression in the sample. Antibodies recognizing the antigen or a portion thereof may be used to create diagnostic immunoassays for detecting antigen released or secreted from living or dying cancer cells in bodily fluids, including but not limited to blood, saliva, urine, pulmonary fluid, or ascites fluid. As discussed in further detail in Examples 4 and 5, below, PIP can bind to adenocarcinomas, carcinomas, sarcomas, or adenosarcomas from tissues including, but not limited to, ovary, breast, lung, prostate, colon, kidney, liver, thyroid, upper digestive tract, and pancreas.

Not all cells in a particular tumor of interest will express PIPA, and cancerous cells in other tissues may express PIPA, thus an individual should be screened for the presence or absence of PIPA on cancerous cells to determine the usefulness of immunotherapy in the individual. The anti-PIPA antibodies, including but not limited to PIP, made by the methods disclosed herein may be used to determine whether an individual diagnosed with cancer may be deemed a candidate for immunotherapy using antibodies directed against PIPA. In one embodiment, a cancerous tumor or a biopsy sample may be tested for expression of PIPA, using antibodies directed against PIPA. Individuals with cancer cells that express PIPA are suitable candidates for immunotherapy using antibodies directed against PIPA. Staining with PIP or a PIP-equivalent antibody may also be used to distinguish cancerous tissues from normal tissues.

Methods of using PIP or equivalent antibodies or polypeptides for diagnostic purposes are useful both before and after any form of anti-cancer treatment, e.g., chemotherapy or radiation therapy, to determine which tumors are most likely to respond to a given treatment, prognosis for an individual with cancer, tumor subtype or origin of metastatic disease, and progression of the disease or response to treatment.

The compositions of this invention are also suitable for diagnosis of disease states other than cancer, using the methods generally described above in application with other diseased (non-cancerous) cells. Disease states suitable for use in the methods of this invention include, but are not limited to, disease or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Uses described anywhere in this application that recite their use for PIP also encompass the use of other PIPA agonists, antagonists and modulators as described herein. In such embodiments, the PIPA agonists, antagonist or other non-antibody modulator is substituted for PIP in the steps described, and alterations within the scope of the ordinarily skilled practitioner are made to tailor the method to the substituted PIPA modulatory composition.

Methods of Using PIP, PIP-equivalent Antibodies or PIP-equivalent Polypeptides for Therapeutic Purposes Monoclonal antibody PIP and equivalent antibodies or polypeptides made by the methods disclosed herein may be used for therapeutic purposes in individuals with cancer of the ovary, breast, lung, prostate, colon, kidney, liver, thyroid, or pancreas. Therapy with PIP can involve formation of complexes either in vitro or in vivo as described above. In one embodiment, monoclonal antibody PIP or PIP equivalent antibody or polypeptide can bind to and reduce the proliferation of cancerous cells (e.g., colon cancer cells or ovarian cancer cells). In another embodiment, monoclonal antibody PIP or a PIP equivalent antibody or polypeptide can bind to and induce apoptotic cell death in the cancer cell. In another embodiment, monoclonal antibody PIP can bind to cancerous cells and delay the development of metastasis. In yet another embodiment, an individual with cancer is given palliative treatment with PIP. Palliative treatment of a cancer patient involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

In yet another embodiment, PIP or PIP equivalent antibodies or polypeptides can bind to cancerous cells and induces an active immune response against the cancerous cells expressing PIPA. In some cases, the active immune response can cause the death of the cancerous cells (e.g., PIP binding to cancer cells inducing apoptotic cell death), or inhibit the growth (e.g., block cells cycle progression) of the cancerous cells. In other cases, PIP can bind to cancerous cells and antibody dependent cellular cytotoxicity (ADCC) can eliminate cancerous cells to which PIP binds.

In some cases, the antibody or polypeptide binding can also activate both cellular and humoral immune responses and recruit more natural killer cells or increased production of cytokines (e.g., IL-2, IFN-γ, IL-12, TNF-α, TNF-β, etc.) that further activate an individual's immune system to destroy cancerous cells. In yet another embodiment, the antibodies or polypeptides can bind to cancerous cells and macrophages or other phagocytic cell can opsonize the cancerous cells.

In yet another embodiment, PIP or PIP equivalent antibodies or polypeptides can be conjugated to a radioactive molecule, toxin (e.g., calicheamicin), or chemotherapeutic molecule or to liposomes or other vesicles containing chemotherapeutic compounds and administered to an individual to target these compounds to the cancer cell containing the antigen recognized by the antibody and thus eliminate cancerous cells. In yet another embodiment, the antibody can be employed as adjuvant therapy at the time of the surgical removal of a cancer expressing the antigen in order to delay the development of metastasis. The antibody can also be administered before surgery (neoadjuvant therapy) in a patient with a tumor expressing the antigen in order to decrease the size of the tumor and thus enable or simplify surgery, spare tissue during surgery, and/or decrease the resulting disfigurement.

Various formulations of PIP and equivalent antibodies or polypeptides may be used for administration. In some embodiments, PIP and PIP equivalent antibodies or polypeptides may be administered neat. In other embodiments, PIP (or PIP equivalents) and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington's Pharmaceutical Sciences* 19th Ed. Mack Publishing (1995).

Generally, these agents are formulated for administration by injection (e.g., intraperitoneally, intravenously, subcutaneously, intramuscularly, etc.), although other forms of administration (e.g., oral, mucosal, etc) can be also used. Accordingly, PIP antibody and equivalents thereof are preferably combined with pharmaceutically acceptable vehicles such as saline, Ringer's solution, dextrose solution, and the like. The particular dosage regimen, ie., dose, timing and repetition, will depend on the particular individual and that individual's medical history. Generally, a dose of at least about 1 μg/kg body weight, at least about 10 μg/kg body weight, at least about 50 μg/kg body weight, at least about 100 μg/kg body weight, at least about 250 μg/kg body weight, at least about 500 μg/kg body weight, at least about 750 μg/kg body weight, at least about 1 mg/kg body weight, at least about 3 mg/kg body weight, at least about 5 mg/kg body weight, or at least about 10 mg/kg body weight is administered. Empirical considerations, such as the half-life, generally will contribute to determination of the dosage. Antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of PIP antibodies may be appropriate. Various formulations and devices for achieving sustained release are known in the art.

In one embodiment, dosages for PIP antibodies or PIP equivalent antibodies or polypeptides may be determined empirically in individuals who have been given one or more administration(s). Individuals are given incremental dosages of PIP. To assess efficacy of PIP or other equivalent antibody or polypeptide, a marker of the specific cancer disease state can be followed. These include direct measurements of tumor size via palpation or visual observation, indirect measurement of tumor size by x-ray or other imaging techniques, an improvement as assessed by direct tumor biopsy and microscopic examination of the tumor sample, the measurement of an indirect tumor marker (e.g., PSA for prostate cancer), a decrease in pain, paralysis, impairment of speech, vision, breathing or other disability associated with the tumor, increased appetite, or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. PIP antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. A mixture of antibodies, as they are often denoted in the art, may be particularly useful in treating a broader range of population of individuals.

Assessment of disease is performed using standard methods in the arts, such as imaging methods and monitoring appropriate marker(s).

Kits Comprising Antibodies or Polypeptides that Bind to PIPA.

The invention also provides kits comprising antibodies or polypeptides that bind to PIPA for use in diagnosis or therapy. Accordingly, the kits comprise an antibody or polypeptide that can bind to PIPA specifically and/or form a complex with PIPA. In some aspects, the binding of an antibody (e.g., monoclonal, polyclonal, human, humanized, etc.) is used for diagnosing cancer in an individual. In other aspects, the kits may be used, for example, to treat an individual with cancer or a family history of cancer. The kits of this invention are in suitable packaging, and may optionally provide additional components such as, buffers and instructions for determining binding to PIPA, such as capture reagents, developing reagents, labels, reacting surfaces, means for detection, control samples, and interpretive information. The instructions may be for any measurement of antigen binding, including, but not limited to, those assays described herein. In some embodiments, reagents described above are supplied such that multiple measurements may be made, such as allowing for measurements in the same individual over time or multiple individuals. Any appropriate means for detecting binding of the antibodies may be employed (and provided in the kits) such as a labeled anti-human antibody, wherein the label may be an enzyme, fluorophore, chemiluminescent material radioisotope or coenzyme. Generally, the label used will be an enzyme.

The following examples are provided to illustrate, but not to limit, the invention.

EXAMPLES

Example 1

Preparation of Human Mullerian Duct-Derived Epithelial Cells as an Immunogen

Human fetal uterus and fallopian tube of gestational age between 17 to 25 weeks were obtained from Advanced Bioscience Research at Alameda county, Calif. The tissues were procured and shipped to the lab in tissue culture medium under wet ice bath. Immediately upon arrival, the tissues were cleaned of excess connective-tissues, carefully separated from ovary and vaginal tissue, and washed five times with fresh tissue culture medium.

The uteri and fallopian tubes were minced with scissors or cut into small pieces (less than 1 mm thick) with a razor blade. The tissue pieces from each set of tissues were plated directly in a T75 flask with 10 ml preferred nutrient medium as disclosed herein. Further dissociation of the ovaries with collagenase-dispase (0.5%) for 30 minutes at 37 C could be done, but the procedure reduced the recovery of Mullerian ductal derived cells. The cells were cultured in F12/DMEM supplemented with 10 μg/ml insulin, transferrin (10 μg/ml), α-tocopherol (5 μg/ml), 10 ng/ml basis fibroblast growth factor, 3 μM forskolin and 0.5% bovine serum albumin in T-75 flasks or 100 mm plates at standard incubation conditions. Under these culture conditions, the human Mullerian ductal epithelial cells attached to the plastic of the tissue culture container and grew out as a monolayer. Cultures were passaged by first incubating the cells in 0.5% collagenase/dispase to detach them from the tissue culture container and then re-plating the cells in the same culture medium at a 1 to 5-split ratio. It usually took 3-4 weeks for subcultured cells to grow to confluence. Cells were used for immunization and antibody screening within three passages.

To harvest the cells, the cells were rinsed once with calcium and magnesium free Hanks' saline solution, incubated in 0.02% EDTA in Hanks' saline solution at 37 C for 15 minutes. The cells were detached from the culture surface by gentle tapping. The cell suspension was precipitated by centrifuge at 1000 rpm for 10 minutes. The supernatant was removed and cells were resuspended in serum free medium (F12/DMEM) containing appropriate non-denaturing adjuvant.

Example 2

Generation of Monoclonal Antibodies Against Human Mullerian Duct-derived Epithelial Cells Approximately $10^6$ human Mullerian duct-derived epithelial cells per mouse were injected into Balb/c mice via footpad, once a week. Non-denaturing adjuvants, (e.g., Ribi) were used. After 6 weeks of weekly injection, a drop of blood was drawn from the tail of each immunized animal to test the titer of antibodies against human Mullerian duct-derived epithelial cells using FACS analysis. When the titer reached at least 1:2000, the mice were sacrificed in a $CO_2$ chamber followed by cervical dislocation. Lymph nodes were harvested for hybridoma preparation.

Lymphocytes from mice with the highest titer were fused with the mouse myeloma line X63-Ag8.653 using 35% polyethylene glycol 4000. On day 10 following the fusion, the hybridoma supernatants were screened for the presence of human Mullerian duct-derived epithelial cell specific monoclonal antibodies by fluorescence activated cell sorting (FACS). Conditioned medium from each hybridoma was incubated for 30 minutes with an aliquot of human Mullerian duct-derived epithelial cells. After incubation, the cell samples were washed, resuspended in 0.1 ml diluent and incubated with 1 μg of FITC conjugated F(ab')$_2$ fragment of goat anti-mouse IgG for 30 min at 4 C. The cells were washed, resuspended in 0.5 ml FACS diluent and analyzed using a FACScan cell sorter (Becton Dickinson; San Jose, Calif.). Hybridoma clones were selected for further expansion, cloning, and characterization based on their binding to the surface of one or more of the cell lines as assessed by FACS. In the current specific instance, one hybridoma was selected making a monoclonal antibody designated PIP which binds an antigen designated PIPA.

Example 3

Screening a Panel of Antibodies Against the Antigen Source

Human Mullerian duct-derived epithelial cells were detached from tissue culture flasks in the presence of 0.5 mM EDTA, centrifuged at 1400 rpm for 5 minutes and resuspended in phosphate buffered saline (PBS) containing 1% bovine serum albumin (BSA) and 2 mM EDTA (FACS diluent). The cells, were counted and adjusted to $10^7$ cells/ml. About 0.1 ml of cells were incubated with 100 μl hybridoma supernatant or 1 μg of purified monoclonal antibodies in 100 μl FACS diluent for 30 min at 4 C. Monoclonal antibodies were purified from tissue culture supernatant using protein-G affinity chromatography. The following materials were used for the antibody purification process: hybridoma tissue culture supernatant, Immunopure (G) IgG binding buffer (Pierce No. 21011 Rockford, Ill.), Immunopure IgG Elution Buffer (Pierce No. 21009), concentrated HCl (for adjusting pH), Corning 1 liter PES (polyether sulfone), 0.22 μm filter (Corning No. 431098, Corning, N.Y.), Amersham Pharmacia GradiFrac System (Amersham Pharmacia, Piscataway, N.J.), Protein-G Sepharose 4 Fast Flow (Amersham Pharmacia No. 17-0618-02), Stripping buffer which is 3M KSCN/50 mM Tris pH 7.8, and PBS (phosphate buffered saline) 3M Tris pH 9.0.

To purify the PIP antibody, the volume of supernatant was measured and an equal volume of binding buffer was added to the supernatant. The mixture was allowed to equilibrate to room temperature. The supernatant was clarified by passage through a 0.22 μm filter. The supernatant was loaded on to a protein-G column using the GradiFrac system. The column was washed with 5-10 column volumes of binding buffer. The monoclonal antibodies were eluted with the elution buffer and 2 ml fractions were collected. An $OD_{280}$ reading of the fractions were obtained and the fractions containing monoclonal antibodies were pooled. The eluted monoclonal antibody fractions were neutralized by adding 1/20 volume of 3M Tris. The sample was dialyzed in 1×PBS at 4 C (with 3 buffer changes of at least 3 hours per change). The purified monoclonal antibodies were sterile filtered (0.2 μM) and stored at 2-8 C.

After purification of the PIP monoclonal antibody from the hybridoma supernatant, it was re-tested for binding to human Mullerian duct-derived epithelial cells. The cell samples were prepared as described above in Example 2 and incubated with the purified antibody at various concentrations After incubation the cells were washed, resuspended in 0.1 ml diluent and incubated with 1 μg of FITC conjugated F(ab')$_2$ fragment of goat anti-mouse IgG for 30 min at 4 C. The cells were washed, resuspended in 0.5 ml FACS diluent and analyzed using a FACScan cell sorter (Becton Dickinson; San Jose, Calif.). A shift to the right on FACScan indicated that the purified antibody still bound to the human Mullerian duct-derived epithelial cells.

Example 4

Immunohistochemistry Methods

Frozen tissues are prepared, sectioned, with or without fixation, and IHC performed by one of a number of methods known to one familiar with the art. Examples are given in Stephan et al. *Dev. Biol.* 212: 264-277 (1999), and Stephan et al. *Endocrinology* 140: 5841-54 (1999), or as follows. Frozen tissue samples were embedded in OCT compound and quick-frozen in isopentane with dry ice. Cryosections were cut with a Leica 3050 CM mictrotome at thickness of 5 μm and thaw-mounted on vectabound-coated slides. The sections were fixed with ethanol at −20 C or 75% acetone(4-8C)/25% ethanol (RT) for 10 minutes and allowed to air-dry overnight at room temperature. The fixed sections were stored at −70 C until use. For immunohistochemistry, the tissue sections were retrieved and first incubated in blocking buffer (PBS, 5% normal goat serum, 0.1% Tween 20, 100 μg/mL Avidin) for 30 minutes at room temperature, and then incubated with the PIP and control monoclonal antibodies (1 to 5 μg/ml) diluted in PBS, 5% normal goat serum, 0.1% Tween at 4 C overnight. The sections were then washed three times with the PBS and incubated for at least 30 minutes in hydrogen peroxide-d-biotin solution (3% hydrogen peroxide, 30 μg/nL d-biotin, in PBS). The bound monoclonal antibodies were detected with a goat anti-mouse IgG+IgM (H+L) F(ab')$^2$-biotin conjugate or horse-anti-mouse IgG H+L conjugate, followed by ABC Elite (Vector Lab catalog no. PK6100) and finally developed in the peroxidase substrate diaminobenzidine (1 mg/ml, Sigma catalog no. D 5637) in 0.1 M sodium acetate buffer pH 5.05 and 0.003% hydrogen peroxide (Sigma catalog no. H1009) or in 0.05M Tris buffer pH 7.6 and 75 μL 3% hydrogen peroxide. The stained slides were counter-stained with hematoxylin or methyl green and examined under a Nikon microscope.

Table 1 shows a panel of normal tissues (tissue nos. 1-21) stained with PIP antibody. Table 2 shows a panel of ovarian cancers (tissue nos. 22-58) stained with PIP antibody. These samples were frozen in OCT and sectioned immediately before use as described above. The sections were incubated with PIP antibody (1 to 5 μg/ml) and secondary antibody as described above. Slides were scored for the presence (+) or absence (−) of PIP signal.

TABLE 1

Binding of PIP to normal tissues by IHC

| TISSUE NO. | TISSUE TYPE | IHC RESULT (PIP reactivity) |
|---|---|---|
| 1 | Adrenal | negative |
| 2 | Blood | +/− |
| 3 | Bone Marrow | negative |
| 4 | Brain (cerebral cortex) | negative |
| 5 | Breast | negative |
| 6 | Colon | negative except ++ surface epithelium |

TABLE 1-continued

Binding of PIP to normal tissues by IHC

| TISSUE NO. | TISSUE TYPE | IHC RESULT (PIP reactivity) |
|---|---|---|
| 7 | Heart | negative |
| 8 | Lung | negative except weak + bronchial epithelium |
| 9 | Kidney | negative except weak + scattered tubules |
| 10 | Liver | negative |
| 11 | Nerve | negative |
| 12 | Ovary | negative except ++ follicular epithelium |
| 13 | Pancreas | negative |
| 14 | Prostate | negative except focal ++ glands |
| 15 | Skeletal muscle | negative |
| 16 | Skin | negative except + sweat glands and sebaceous glands |
| 17 | Small intestine | negative except + surface epithelium |
| 18 | Spleen | negative |
| 19 | Stomach | negative except variable ++ on mid-surface epithelium |
| 20 | Thyroid | negative |
| 21 | Uterus | negative except focal +/++ surface epithelium |

TABLE 2

Binding of PIP to ovarian cancers by IHC

| TISSUE NO. | TISSUE TYPE | DIFFERENTIATION | IHC RESULT (PIP reactivity) |
|---|---|---|---|
| 22 | Metastatic | | − |
| 23 | Metastatic | | − |
| 24 | Metastatic | | − |
| 25 | Metastatic | | − |
| 26 | Mucinous | | − |
| 27 | Serous | poor specimen | − |
| 28 | Serous | | +/++[a] |
| 29 | Serous | intermediate | +[a] |
| 30 | Serous | intermediate | ++ |
| 31 | Serous | intermediate | +/++[a] |
| 32 | Serous | intermediate | ++[a] |
| 33 | Serous | low | − |
| 34 | Serous | high | ++ |
| 35 | Serous | | − |
| 36 | Serous | low | − |
| 37 | Serous | low | ++ |
| 38 | Serous | — | ++ |
| 39 | Serous | low | +++ |
| 40 | Serous | low to intermediate | +[a] |
| 41 | Mucinous | low | − |
| 42 | Endometrioid | low | − |
| 43 | Serous borderline | | ++ |
| 44 | Serous borderline | | ++ |
| 45 | Serous papillary | | ++[a] |
| 46 | Serous papillary | | ++[a] |
| 47 | Serous papillary | | ++[a] |
| 48 | Serous papillary | | ++[a] |
| 49 | Serous papillary | | − |
| 50 | Adenocarcinoma | | − |
| 51 | Adenocarcinoma | | ++[a] |
| 52 | Adenocarcinoma | | +[a] |
| 53 | Serous cystadenoma | | ++ |
| 54 | Clear cell carcinoma | | ++ |
| 55 | Clear cell carcinoma | | ++[a] |
| 56 | Endometriod adenocarcinoma | | ++ |
| 57 | Endometriod adenocarcinoma | | ++[a] |
| 58 | Endometriod adenocarcinoma | | ++[a] |

[a]Staining of sample was heterogeneous.

TABLE 3

Binding of PIP to metastatic tumors

| TISSUE NO. | TISSUE TYPE | IHC RESULT (PIP reactivity) |
|---|---|---|
| 59 | Metastatic Breast carcinoma | + |
| 60 | Metastatic Renal carcinoma | +/− |
| 61 | Metastatic Breast Carcinoma | − |
| 62 | Metastatic Ewing's Sarcoma | − |
| 63 | Metastatic Renal Carcinoma | − |
| 64 | Metastatic Breast Carcinoma | − |
| 65 | Metastatic Renal carcinoma | + |
| 66 | Metastatic Lung carcinoma | − |
| 67 | Metastatic Lung Carcinoma (Met Small Cell) | − |
| 68 | Metastatic Breast Carcinoma | + |
| 69 | Metastatic Breast Carcinoma | + |
| 70 | Metastatic (Upper G.I. Carcinoma) | − |
| 71 | Metastatic Breast Carcinoma | − |
| 72 | Metastatic Renal Carcinoma | + |
| 73 | Metastatic Breast Carcinoma | − |
| 74 | Metastatic Bronchial/Oesophageal Carcinoma | + |
| 75 | Metastatic Breast Carcinoma | + |
| 76 | Metastatic Renal Carcinoma | − |
| 77 | Metastatic Thyroid Carcinoma | − |
| 78 | Metastatic Renal Carcinoma | +/− |
| 79 | Metastatic Prostatic Carcinoma | − |
| 80 | Metastatic Breast Carcinoma | − |
| 81 | Metastatic Renal Carcinoma | − |
| 82 | Metastatic Breast Carcinoma | − |
| 83 | Metastatic Hypernephroma | + |
| 84 | Metastatic Breast Carcinoma | − |
| 85 | Metastatic Breast Carcinoma | − |
| 86 | Metastatic hepatocellular carcinoma. | − |
| 87 | Metastatic renal carcinoma | − |
| 88 | Metastatic breast carcinoma | − |
| 89 | Metastatic prostate adenocarcinoma | − |
| 90 | Metastatic large cell carcinoma, most likely from a lung primary carcinoma. | − |
| 91 | Metastatic Breast adenocarcinoma. | + |
| 92 | Metastatic breast adenocarcinoma, | +/− |
| 93 | Metastatic adeno-squamous carcinoma, in keeping with a bronchogenic primary. | + |
| 94 | metastatic renal cell carcinoma. | + |
| 95 | metastatic adenocarcinoma. | +/− |
| 96 | Metastatic high grade osteoblastic osteosarcoma | − |

+/−: equivocal

FIG. 1 also shows results from immunohistochemistry staining for PIP binding in ovarian cancer tissues. The numbers on the panels refer to the tissue number in Table 2. Ovarian carcinomas showed strong uniform staining in cancerous epithelial cells (tissue numbers 30, 34, 37, 38, 39). Staining of some clusters of tumor cells, but not others, was seen in tissue number 29.

Example 5

Immunohistochemical Detection of PIPA Expression in Colon Cancer Cell Line

Colon cancer cell line, HT-29 (ATCC No. HTB-38) was cultured in F12/DMEM medium supplemented with 5% fetal bovine serum. Confluent cell cultures were rinsed in PBS and incubated in PBS with 0.02% EDTA at 37 C for 15 minutes. This cells were detached from the substrate by gentle shaking. The cell suspension was precipitated by centrifuge at 1000 rpm for 10 minutes. The supernatant was aspirated and the cell pellet was frozen in OCT in dry ice/isobutane bath. The frozen block was section with a cryo-microtome and the sections were mounted onto microscopic slides as for frozen tissue sections. For immunohistochemistry, the sections were first incubated in blocking buffer (PBS, 5% normal goat serum, 0.1% Tween 20) for 30 minutes at room temperature, and then incubated with the PIP antibody and control monoclonal antibodies diluted in blocking buffer (5 µg/ml) for 120 minutes. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counterstained with hematoxylin and examined under Nikon microscope. The results are shown in FIG. 2. Strong staining to the colon cancer tissue by PIP was observed (FIG. 2B). No positive staining was seen in control slides (FIG. 2A), where no PIP was added.

Example 6

Binding of PIP to Normal Tissues

Normal tissue were frozen and mounted as with tumor tissues. Cryosections were cut with a Leica 3050 CM mictrotome at thickness of 5 µm and thaw-mounted on vectabond-coated slides. The sections were fixed with either ethanol at −20 C or a 75% Acetone(4-8C)/25% ethanol (RT) mixture and allowed to air-dry overnight at room temperature. Primary antibody PIP was used at a final concentration between 1 and 5 µg/ml. Staining and detection protocols were identical to those described in Example 4, above.

Figure 3:
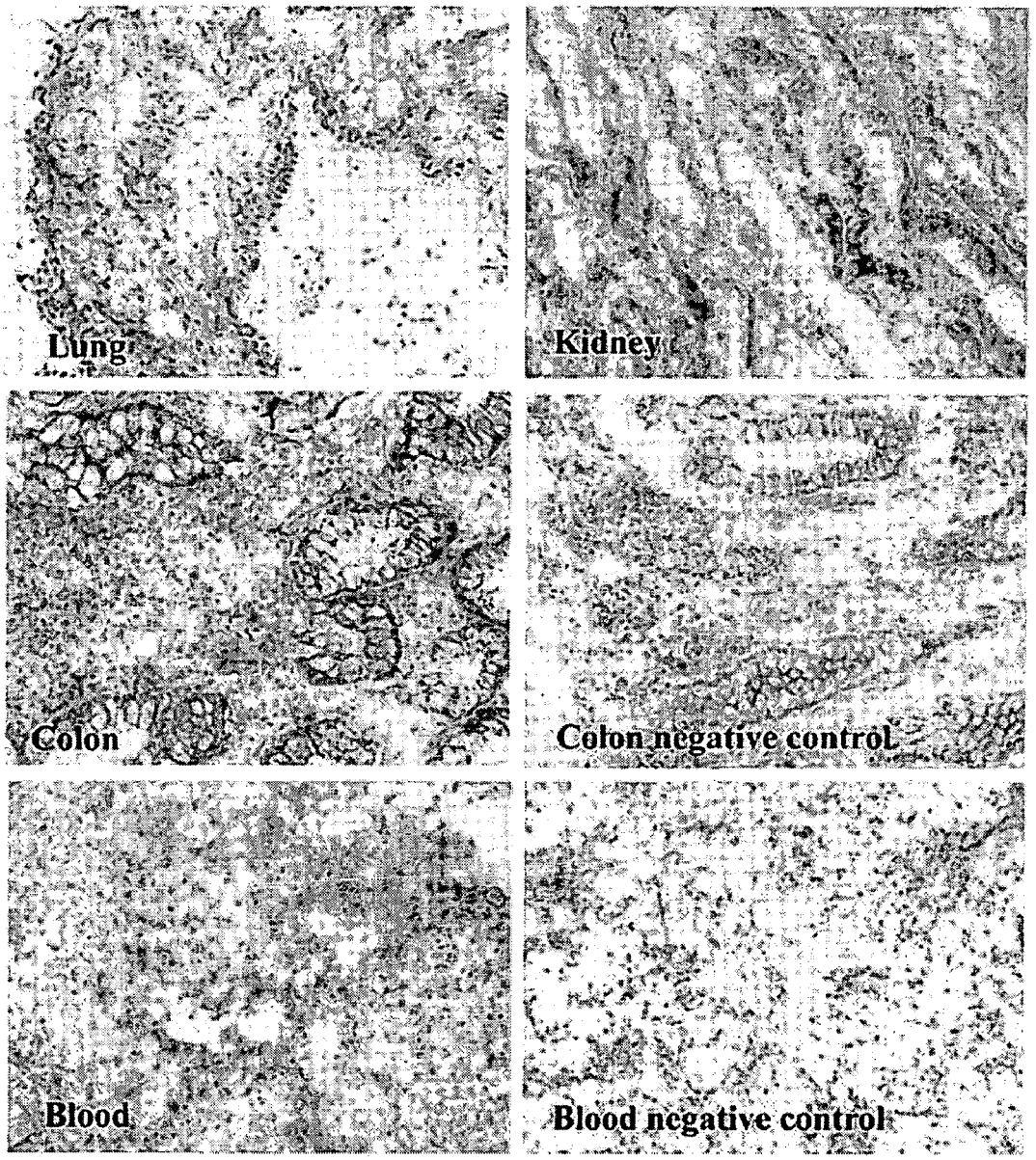
FIG. 3 shows photographs of immunohistochemical staining of normal tissue samples.

Experiments were performed on one or two separate normal tissue samples. When two separate samples were used, they were obtained from two separate patients and showed the same results. Negative controls in which no PIP was added to the tissue samples or an isotype matched negative control were also included in the experiments. FIG. 3 shows the results from the one set of the samples. The results of the experiments with normal tissue samples are also shown in Table 1, above (tissue nos. 1-21).

Example 7

Binding of PIP to Metastatic Tumor Tissues

Metastatic tumors were frozen and mounted as with normal tissues. Cryosections were cut with a mictrotome at thickness of 5 µm and thaw-mounted on coated slides. The sections were fixed with ethanol or acetone and allowed to air-dry overnight at room temperature. Sections were stored at −20C until use. Sections were removed from the freezer, allowed to reach room temperature, and washed in 0.1 M Tris buffered saline (TBS) at pH 7.6. Primary antibody PIP was applied at a final concentration between 1 and 5 µg/ml, and slides were incubated at room temperature (RT) for 60 minutes. Slides were washed with TBS, incubated with the Link antibody (LSAB+kit, Dako) at RT for 30 minutes, and washed again. Slides were then incubated with streptavidin peroxidase conjugate for 30 minutes at RT and washed. Slides were developed with 1.0 mL Chromagen Solution A and 20 µL Chromagen Solution B (LSAB+kit, Dako) for 10 minutes, washed, counterstained in Mayer's hematoxylin, dehydrated, and mounted for viewing. The results from staining of metastatic tumors are listed in Table 3.

Example 8

In vitro Effects of PIP Antibody

The effects of PIP antibody on cell proliferation were measured using the OV90 cell line in an MTT assay. This cell line has been shown to express PIPA through various protein chemistry assays, including Western blots and FACS analysis using the PIP antibody. The cells were removed from stock flasks with 10 mM EDTA and centrifuged. The cells are resuspended and plated at 5000 cells/well in 96 well plates. PIP antibody is added to the cells at varying concentrations, ranging from 0.02 µg/ml to 20 µg/ml. The cells were allowed to proliferate for four days (4) in a 37 C incubator. At the end of four days, a 1:10 dilution of a MTT solution (5 mg/ml in PBS) is added to the medium in the wells. The cells were incubated for 4 hours at 37 C. The medium in the wells is removed and replaced with 100 µl DMSO. After the blue crystals that formed in the cells by MTT uptake are completely dissolved by gentle shaking, the plate is read on a plate reader at 540 nm. After 4 days, OV90 cells incubated with PIP antibody showed no difference in proliferation as compared to control.

In order to further characterize the in vitro activity of PIP antibody, internalization assays were performed using MAb-ZAP (Advanced Targeting Systems). MAb-ZAP comprises of saporin, an agent that stops protein synthesis, which is cross-linked to a secondary antibody that will bind to the primary antibody of choice. If the primary antibody is internalized into the cell, the MAb-ZAP will stop cell proliferation.

Figure 6:
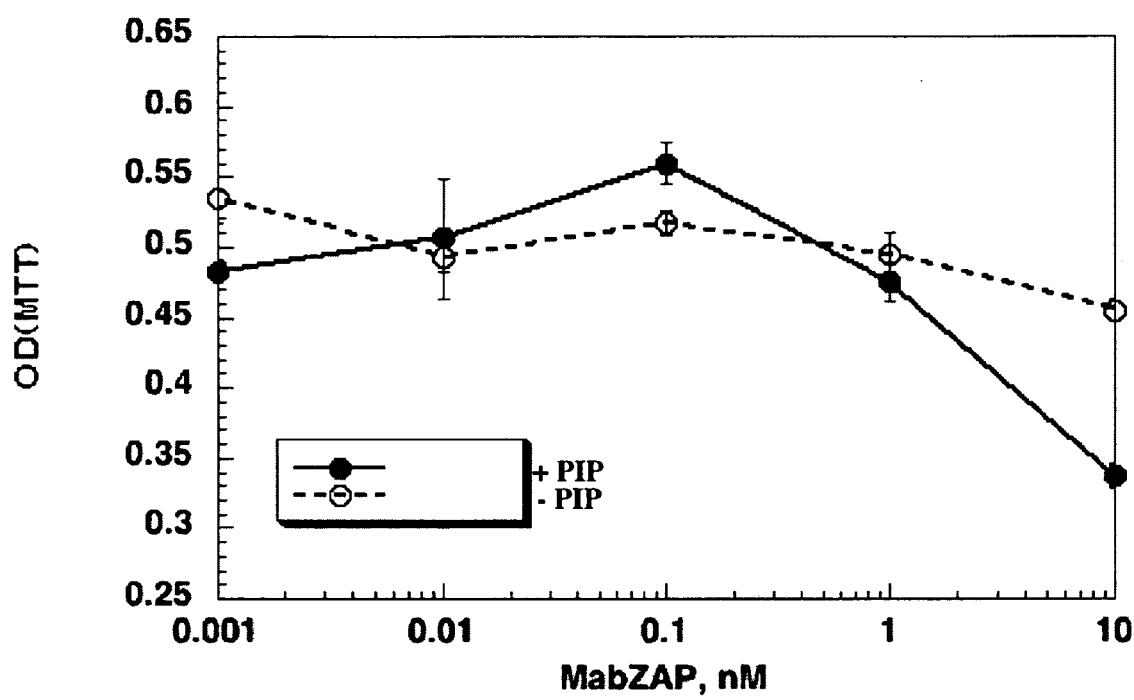
FIG. 6 shows PIP antibody internalization into OV90 cells in vitro.

OV90 cells were removed from stock flasks with 10 mM EDTA and centrifuged. The cells were resuspended at 50,000 cells/ml in the appropriate cell culture medium and 100 µl of the cell suspended was plated per well in 96 well plates. PIP antibody was added immediately to the appropriate wells as 10× concentrates. The final concentration of PIP antibody per well was 10 µg/ml. After 15 minutes at room temperature, MAb-ZAP is added to the appropriate wells as a 10× concentrate. The final MAb-ZAP concentration ranges from 0.001 nM to 10 nM. After 4 days of growth, MTT is added (stock 5 mg/ml in PBS) in a 1:10 dilution per well. Cell proliferation was measured using the methods as described above. The internalization results are shown in FIG. 6. Internalization is observed at a MAb-ZAP concentration range of 1-10 nM. At a concentration of 10 nM of MAb-ZAP, cell proliferation is reduced by approximately 50 percent. This data suggests that the PIP antibody is being internalized in vitro.

Example 9

In vivo Effects of PIP Antibody Conjugated to a Toxin

The in vivo effects of PIP antibody linked to a toxin were studied using a xenograft model in SCID mice. Xenograft tumor models in SCID mice are well known in the art. Briefly, SCID mice were inoculated subcutaneously with 1×10$^7$ OV90 cells. The mice were divided into three treatment groups consisting of control, 150 µg/kg PIP-toxin antibody, and 250 µg/kg PIP-toxin antibody. The treatments were given intravenously and the tumor volume and total body weight of each mouse was measured every four days for 36 days total. The mice in the 250 µg/kg PIP-toxin antibody dose were sacrificed after 13 days due to drastic weight loss. The mice in the control group were sacrificed after 28 days due to increasing tumor burden. Complete tumor regression was observed with the 150 µg/kg dose with no evidence of non-specific toxicity was seen as judged by the lack of weight loss of the mice in this treatment group. This data is consistent with the in vitro data showing internalization of the PIP antibody by OV90 cells.

Example 10

Determination of the Molecular Weight of the Target Antigen PIPA

The antigen PIPA was purified from confluent HT-29 cultures using standard immunoprecipitation methods. The commercially available human colon adenocarcinoma cell line, HT-29 (American Type Culture Collection, Cat. No. HTB-38) was grown in a 1:1 mixture of F12 medium (GibcoBRL, Cat. No. 21700-091) and DMEM medium (GibcoBRL, Cat. No. 12100-061) containing L-glutamine and 10% fetal bovine serum. The cells were grown to confluency in a 37° C. incubator with 5% $CO_2$. In brief, a confluent 175 $cm^2$ culture of HT-29 cells were washed with Hanks' Balanced Salt Solution (HBSS, Sigma Chemicals, St. Louis, Mo.) three times before and were collected by cell scraping in lysis buffer (HBSS containing 2% Triton X-100, 2 mM PMSF, 0.05% $NaN_3$ and 1 tablet per 5 ml of Complete Mini-EDTA free protease tablet; all material obtained from Sigma Chemicals, St. Louis, Mo. except for the Complete Mini-EDTA tree protease tablet, obtained from Roche Molecular Biochemicals). The lysis buffer was used at 1 ml per 175 $cm^2$. The lysate was clarified by centrifugation at 24,000-xg for 45 minutes at 4° C. Clarified lysate was then pre-cleared over protein G sepharose (PG, Amersham Pharmacia, Trenton, N.J.) at 100 µl/175 $cm^2$ cell lysate for 2 hours at 4° C. Pre-cleared lysate was then exposed to 5 µg PIP antibody and 10 µl PG per 175 $cm^2$ cell lysate for 2 hours at 4° C. The PIP/PG was then removed from the cell lysate and washed three times with lysis buffer before elution and analysis. Elution was performed by the addition of 40 µl of sample buffer per 10 µl of PIP/PG and boiling for three minutes. Eluted sample was analyzed on a 4-20% Tris-Glycine gel (Invitrogen) under reducing (sample buffer containing 20 mM DTT) or non-reducing (sample buffer containing 40 mM iodoacetamide) conditions. Gels were subsequently transferred onto nitrocellulose and the purified protein is then analyzed by western blotting with PIP or control mouse IgG.

Figure 5:
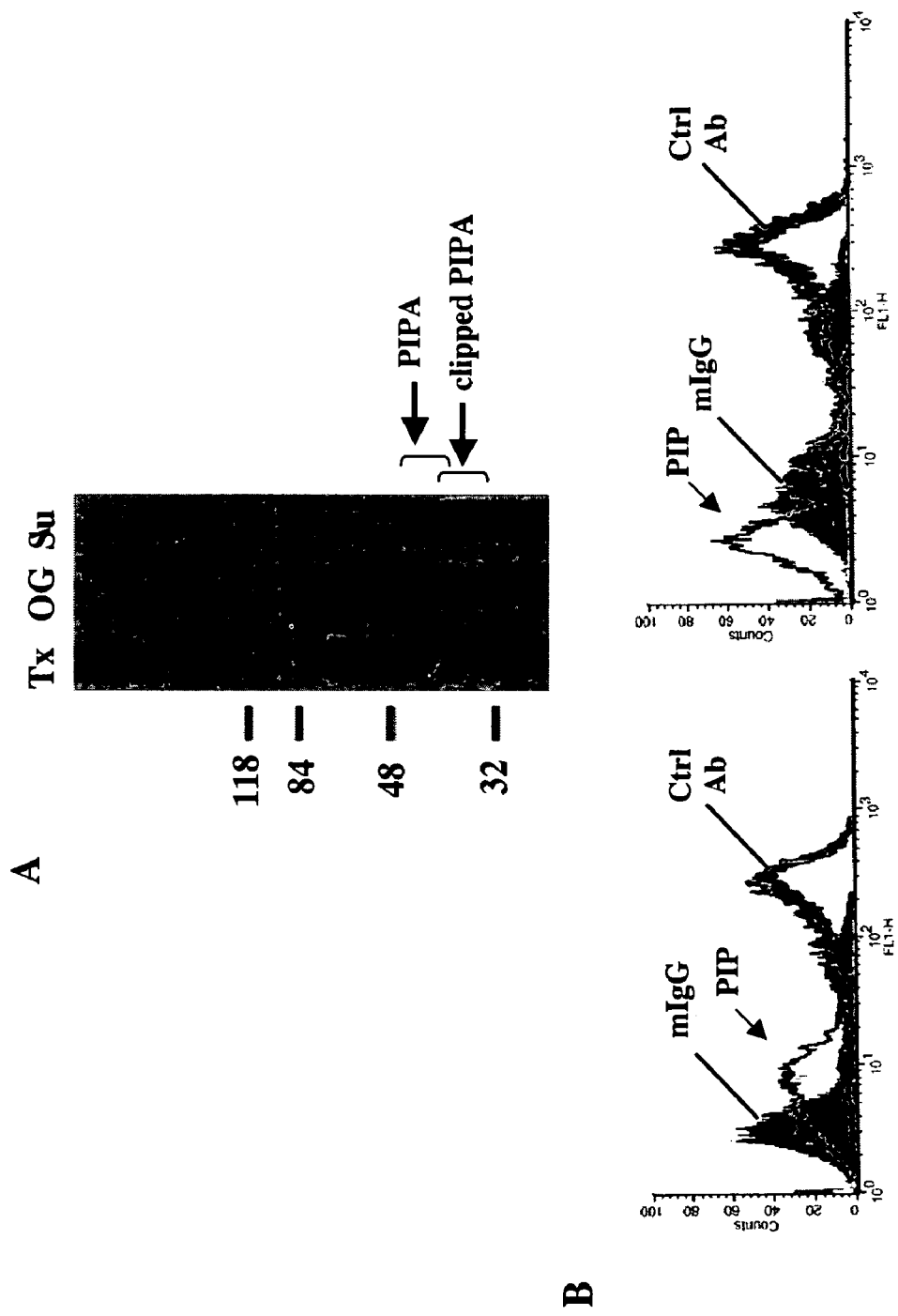
FIG. 5A shows a Western blot of PIPA using PIP antibody. PIPA appears as a smear indicative of glycoproteins at the molecular weight range of 45-50 kD. PIPA appears to be a GPI-linked glycoprotein as seen in FIG. 5B in the FACS analysis of Colo205 cells treated with phosphatidylinositol-specific phospolipase C treatment.

By Western blotting, it was concluded that PIPA is a glycoprotein of approximately 45 kD when reduced and 50 kD when not reduced. FIG. 5 panel A shows a Western blot of PIPA from cells solubilized in 2% TritonX-100, as described above, PIPA from the Triton-X insoluble pellet that is further treated with 20% n-Octylglucoside (OG), and PIPA from cell culture supernatant. PIPA from the TritonX-100 fraction appears as a 45-50 kD smear, indicative of a glycoprotein. PIPA from the OG fraction appears as a broader smear due to the OG treatment of the TritonX-100 insoluble fraction. PIPA from cell supernatant appear as a glycoprotein smear, but at a lower molecular weight. It is believed that this fraction is smaller due to clipping and release from the cellular membrane.

Example 11

Characterization of Antigen PIP

To identify the antigen to which PIP was reactive, an immunoprecipitation experiment was performed. For the immunoprecipitation, thirty 175 $cm^2$ flasks of HT-29 cells (ATCC No. HTB-38) were lysed with a total of 30 ml of lysis buffer (1 ml per 175 $cm^2$ flask). The lysis buffer consisted of Hanks' Balanced Salt Solution (HBSS) fortified with 2% Triton X-100, protease inhibitor cocktail (1 tablet per 5 ml lysis buffer of Complete Mini EDTA-free Protease Inhibitor Cocktail from Roche Molecular Biochemicals, Indianapolis, Ind.), 0.1% sodium azide ($NaN_3$), and 2 mM PMSF. The cell lysate was clarified at 24,000×g for 30 minutes at 4° C. before being passed over a column consisting of 2 mg/ml mouse IgG-conjugated CNBr 6MB sepharose beads (Amersham Pharmacia, N.J.). The resulting lysate was deemed pre-cleared. The pre-cleared HT-29 lysate was then passed over a PIP-conjugated CNBr sepharose 6MB column. The PIP column was conjugated at 1 mg PIP per ml of swollen CNBr 6 MB sepharose beads. The beads (both mouse IgG and PIP) were then washed three times with lysis buffer before elution with 0.1M glycine, pH 2.5. Eluates were collected at 1 column volume fractions and neutralized with a final concentration of 0.1M Tris, pH 8.0, resulting in a final pH of ~7.2. Neutralized fractions were then concentrated to 10% of fraction volume with micro concentrators (Centricon 10 from Millipore, Bedford, Mass.). 10% of the concentrated eluate was then resolved by SDS-PAGE and western blotting. At the same time, 30% of the eluate was further concentrated to a volume compatible for SDS-PAGE and resolved through coomassie staining.

By Western blotting the alkylated PIP and mouse IgG eluate against PIP, glycosylated protein unique to the PIP eluate (>50 kD) was observed. By coomassie staining, there was observed to be a very faint but PIP-unique smear typical of glycoproteins at ~50 kD. This faint band was subsequently excised.

The immunoprecipitation experiment can be repeated or increased in scale until a sufficient sample of PIPA is obtained. The sample can then be submitted for analysis by mass spectrometry.

Example 12

PIPA is a GPI-linked Glycoprotein

To further characterize PIPA, phosphatidylinositol-specific phospholipase C (PI-PLC) treatment was performed. Glycophosphoinositol (GPI) linkage is one of the methods in which a cell attaches proteins to its cellular membrane. These proteins are not imbedded into the cellular membrane, but are instead attached via the GPI anchor to the surface of the cell membrane. Proteins with this GPI anchor can be released from the cells through clipping of the anchor. PI-PLC is specific for the GPI anchor and in vitro experiments can be performed with this enzyme in order to characterize a protein of interest.

Colo205 cells were grown to confluency in F12/DME (50:50 v/v) medium with 10% fetal bovine serum (FBS) in T175 culture flasks. The media was removed by aspiration and the remaining cells washed three times with Hank's Balanced Salt Solution without calcium, magnesium, phenol red, or sodium bicarbonate (HBSS-, Sigma-Aldrich). The washed cells were then dislodged using 10 mM EDTA in HBSS- at 37 C for 12 minutes. The EDTA lifted cells were removed from the flask, diluted 1:1 (v/v) with Hank's Balanced Salt Solution without phenol red or sodium bicarbonate (HBSS+), pelleted and washed three times with HBSS+. The washed cells were split into two conditions. Condition 1 was allowed to incubate with 5 ml HBSS+ containing 5 units phosphatidylinositol-specific phospholipase C (PI-PLC) for 2 hours at room temperature. Condition 2 was allowed to incubate with 5 ml HBSS+ at 2 hours at room temperature. At the end of the incubations, the cells were pelleted and washed with HBSS+ 3 times. Both conditions are then blocked in 1 ml HBSS+ containing 1% BSA and 0.1% sodium azide (blocking buffer) for 30 minutes at 4 C. After blocking, the cells are pelleted, and each split again to three. Each third was incubated with 100 μl blocking buffer containing 2 μg mouse IgG, 2 μg PIP, or 2 μg of control antibody (a monoclonal antibody to a non-GPI-linked membrane protein) for 30 minutes at 4 C. All of the treatment conditions were then resuspended in 100 μl blocking buffer containing 5 μg FITC-conjugated goat anti-mouse IgG (heavy and light chain) for 30 minutes at 4 C. The cells are then washed with 3 ml blocking buffer, pelleted and resuspended in 500 μl blocking buffer for analysis by flow cytometric techniques using standard protocols that are well known in the art. FIG. 5 panel B shows the results of this experiment.

The panel on the left shows the cellular profile without PI-PLC treatment. The panel on the right shows the cellular profile with PI-PLC treatment. As noted with the arrows, the PIPA-expressing population of cells shifts to the left after PI-PLC treatment. This shift represents a loss of PIPA-expressing after the treatment. The PI-PLC clips GPI-linked proteins and releases them from the cellular membrane. The control antibody shows no change upon PI-PLC treatment as expected because its antigen target is not GPI-linked.

Example 13

Other Characterization Experiments to Identify Antigen

Expression cloning is performed as described in Stephan et al. *Dev. Biol.* 212: 264-277 (1999), and Stephan et al. *Endocrinology* 140: 5841-54 (1999). A suitable source for making a library to clone is a tumor tissue or tumor cell line that binds PIP. These include, but are not limited to HT29 or Mullerian duct-derived epithelial cells.

We claim:

1. An isolated antibody PIP produced by a host cell with a deposit number of ATCC No. PTA-4220.

2. A single-chain Fv comprising the variable regions of the light and heavy chains of the antibody PIP of claim 1, wherein said single-chain Fv has the binding specificity of said antibody PIP.

3. A chimeric antibody comprising the variable regions of the light chain and the heavy chain of the antibody PIP of claim 1 and constant regions of the light chain and the heavy chain of a human antibody, wherein said chimeric antibody has the binding specificity of said antibody PIP.

4. A composition comprising the antibody of claim 3, wherein the antibody is linked to a therapeutic agent.

5. A pharmaceutical composition comprising the antibody of claim 3 and a pharmaceutically acceptable excipient, wherein the antibody is linked to a therapeutic agent.

6. A fragment of the chimeric antibody according to claim 3, wherein said fragment has the binding specificity of said antibody PIP.

7. A pharmaceutical composition comprising a therapeutically effective dose of the antibody of claim 3, linked or bound to a therapeutic moiety, and a pharmaceutically acceptable carrier.

8. A humanized antibody comprising each of three CDRs from the light chain of the antibody PIP of claim 1 and each of three CDRs from the heavy chain of the antibody of PIP of claim 1, wherein said humanized antibody has the binding specificity of said antibody PIP.

9. A composition comprising the antibody of claim 8, wherein the antibody is linked to a therapeutic agent.

10. A pharmaceutical composition comprising the antibody of claim 8 and a pharmaceutically acceptable excipient, wherein the antibody is linked to a therapeutic agent.

11. A fragment of the humanized antibody according to claim 8, wherein said fragment has the binding specificity of said antibody PIP.

12. A pharmaceutical composition comprising a therapeutically effective dose of the antibody of claim 8, linked or bound to a therapeutic moiety, and a pharmaceutically acceptable carrier.

13. A method of generating an antibody, comprising expressing one or more polynucleotides encoding the antibody of claim 3 or claim 8 respectively, and purifying the antibody, thereby generating the antibody.

14. A kit comprising an antibody according to any one of claims 1, 3, and 8.

15. An isolated nucleic acid comprising a polynucleotide sequence coding for the antibody of any one of claims 1, 3, 8, or an antigen-binding fragment thereof.

16. The nucleic acid of claim 15, wherein the nucleic acid is operably linked to a promoter.

17. The nucleic acid of claim 16, wherein the promoter and the nucleic acid are contained in an expression vector.

18. A cultured cell line transfected, transformed or infected with a vector containing the nucleic acid of claim 15.

19. A method of producing a substantially purified immunoglobulin polypeptide, or an antigen binding fragment thereof, comprising the steps of:
   a. growing a cell line transformed with the nucleic acid of claim 15 under conditions in which an immunoglobulin polypeptide or antigen binding fragment is expressed; and
   b. harvesting the expressed immunoglobulin polypeptide or fragment.

20. A fragment of the PIP antibody of claim 1, wherein the fragment comprises the variable region of the heavy chain and the variable region of the light chain of said antibody PIP, and wherein said fragment has the binding specificity of said antibody PIP.

21. A pharmaceutical composition comprising a therapeutically effective dose of the fragment of the antibody of claim 20, linked or bound to a therapeutic moiety, and a pharmaceutically acceptable carrier.

22. A method of generating an antibody fragment comprising expressing one or more polynucleotides encoding the fragment of claim 20, and purifying the fragment, thereby generating the fragment.

23. The fragment of claim 20, wherein the fragment is a Fab.

24. The fragment of claim 20, wherein the fragment is a Fab'.

25. The fragment of claim 20, wherein the fragment is a F(ab')$_2$.

26. The fragment of claim 20, wherein the fragment is a Fv.

27. A composition comprising the fragment of any one of claims 20, 6, and 11, 23-26 wherein the fragment is linked to a therapeutic agent.

28. A kit comprising the fragment according to any one of claims 20, 6, and 11, 23-26.

29. The antibody of claim 1, wherein said antibody has the ability to bind to an antigen target that is exposed on the surface of a living cell in vitro or in vivo.

30. A pharmaceutical composition comprising a therapeutically effective dose of the purified antibody of claim 1 or an antigen-binding fragment thereof, linked or bound to a therapeutic moiety, together with a pharmaceutically acceptable carrier.

31. A pharmaceutical composition comprising a therapeutically effective dose of the antibody PIP of claim 1, linked or bound to a therapeutic moiety, and a pharmaceutically acceptable carrier.

32. An isolated nucleic acid comprising a polynucleotide sequence coding for the monoclonal antibody of claim 1 or an antigen binding fragment thereof.

33. A method of producing a substantially purified immunoglobulin polypeptide, or an antigen binding fragment thereof, comprising the steps of:
   a. growing a cell line transformed with the nucleic acid of claim 32 under conditions in which an immunoglobulin polypeptide or antigen binding fragment is expressed; and
   b. harvesting the expressed immunoglobulin polypeptide or fragment.

34. The antibody of claim 1, wherein said antibody has the ability to bind to an antigen target on a cancer cell.

35. The antibody of claim 34, wherein said cancer cell is selected from the group consisting of cancer cells from adrenal gland tumors, AIDS-associated cancers, alveolar soft part sarcoma, astrocytic tumors, bladder cancer, bone cancer, brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer, leukemias, lipoma/benign lipomatous tumors, liposarcoma/malignant lipomatous tumors, liver cancer, lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, pheochromocytoma, pituitary tumors, prostate cancer, posterior uveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers.

36. The antibody of claim 35, wherein the bladder cancer is selected from the group consisting of squamous cell carcinoma and transitional cell carcinoma.

37. The antibody of claim 35, wherein the bone cancer is selected from the group consisting of admantinoma, aneurismal bone cysts, osteochondroma and osteosarcoma.

38. The antibody of claim 35, wherein the kidney cancer is selected from the group consisting of nephroblastoma and papillary renal cell carcinoma.

39. The antibody of claim 35, wherein the liver cancer is selected from the group consisting of hepatoblastoma and hepatocellular carcinoma.

40. The antibody of claim 35, wherein the uterine caner is selected from the group consisting of carcinoma of the cervix, endometrial carcinoma and leiomyoma.

41. An isolated cell line having a deposit number of ATCC No. PTA-4220.

42. A method of generating antibody PIP comprising culturing the isolated cell line according to claim 41 under conditions that allow production of antibody PIP, and purifying the antibody, thereby generating antibody PIP.

* * * * *

SEQUENCE LISTING

```
<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 358
<212> TYPE: DNA
<213> ORGANISM: Mus Musculus

<400> SEQUENCE: 2
gatgtgcagc ttcaggagtc aggacctgac ctggtgaaac cttctcagtc agtttcactc      60
acctgcactg tcactggcta ctccatcacc agtggttatg gctggcactg gatccggcag     120
tttccaggaa ataaactgga atggatgggc tgcatacact acagtggtag cactaactac     180
aacccatctc tcaaaagtcg aatctctgtc actcgagaca catccaagaa ccagttcttc     240
ctgcagttga attctgtgac tactgaggac acagccacat attactgtgc aagaagggaa     300
tatggtaact atgctatgga ctactggggt caaggaacct cagtcaccgt ctcctcag      358

<210> SEQ ID NO 3
<211> LENGTH: 119
<212> TYPE: PRT
<213> ORGANISM: Mus Musculus

<400> SEQUENCE: 3

Asp Val Gln Leu Gln Glu Ser Gly Pro Asp Leu Val Lys Pro Ser Gln
1               5                   10                  15

Ser Val Ser Leu Thr Cys Thr Val Thr Gly Tyr Ser Ile Thr Ser Gly
            20                  25                  30

Tyr Gly Trp His Trp Ile Arg Gln Phe Pro Gly Asn Lys Leu Glu Trp
        35                  40                  45

Met Gly Cys Ile His Tyr Ser Gly Ser Thr Asn Tyr Asn Pro Ser Leu
    50                  55                  60

Lys Ser Arg Ile Ser Val Thr Arg Asp Thr Ser Lys Asn Gln Phe Phe
```

```
                65                  70                  75                  80
Leu Gln Leu Asn Ser Val Thr Thr Glu Asp Thr Ala Thr Tyr Tyr Cys
                    85                  90                  95
Ala Arg Arg Glu Tyr Gly Asn Tyr Ala Met Asp Tyr Trp Gly Gln Gly
            100                 105                 110
Thr Ser Val Thr Val Ser Ser
        115

<210> SEQ ID NO 4
<211> LENGTH: 54
<212> TYPE: DNA
<213> ORGANISM: Mus Musculus

<400> SEQUENCE: 4
atgagagtgc tgattctttt gtgcctgttc acagcctttc ctggtatcct gtct         54

<210> SEQ ID NO 5
<211> LENGTH: 18
<212> TYPE: PRT
<213> ORGANISM: Mus Musculus

<400> SEQUENCE: 5

Met Arg Val Leu Ile Leu Leu Cys Leu Phe Thr Ala Phe Pro Gly Ile
1               5                   10                  15
Leu Ser

<210> SEQ ID NO 6
<211> LENGTH: 340
<212> TYPE: DNA
<213> ORGANISM: Mus Musculus

<400> SEQUENCE: 6
gacattgtga tgacacagtc tccatcctcc ctgagtgtgt cagcaggaga gaaggtcact    60
atgagctgca agtccagtca gagtctgtta acagtggaa atcaaaagaa ctacttggcc    120
tggtaccagc agaaaccagg gcagcctcct aaactgttga tctacggggc atccactagg    180
gaatctgggg tccctgatcg cttcacaggc agtggatctg gaaccgattt cactcttacc    240
atcagcagtg tgcaggctga agacctggca gtttattact gtcagaatga tcatagttat    300
ccattcacgt tcggctcggg gacaaagttg gaattaaaac                        340

<210> SEQ ID NO 7
<211> LENGTH: 119
<212> TYPE: PRT
<213> ORGANISM: Mus Musculus

<400> SEQUENCE: 7

Asp Val Gln Leu Gln Glu Ser Gly Pro Asp Leu Val Lys Pro Ser Gln
1               5                   10                  15
Ser Val Ser Leu Thr Cys Thr Val Thr Gly Tyr Ser Ile Thr Ser Gly
                20                  25                  30
Tyr Gly Trp His Trp Ile Arg Gln Phe Pro Gly Asn Lys Leu Glu Trp
            35                  40                  45
Met Gly Cys Ile His Tyr Ser Gly Ser Thr Asn Tyr Asn Pro Ser Leu
        50                  55                  60
Lys Ser Arg Ile Ser Val Thr Arg Asp Thr Ser Lys Asn Gln Phe Phe
65                  70                  75                  80
Leu Gln Leu Asn Ser Val Thr Thr Glu Asp Thr Ala Thr Tyr Tyr Cys
                85                  90                  95
```

```
Ala Arg Arg Glu Tyr Gly Asn Tyr Ala Met Asp Tyr Trp Gln Gly
            100                 105                 110

Thr Ser Val Thr Val Ser Ser
        115

<210> SEQ ID NO 8
<211> LENGTH: 60
<212> TYPE: DNA
<213> ORGANISM: Mus Musculus

<400> SEQUENCE: 8
atggaatcac agactcaggt cctcatctcc ttgctgttct gggtatctgg tacctgtggg      60

<210> SEQ ID NO 9
<211> LENGTH: 20
<212> TYPE: PRT
<213> ORGANISM: Mus Musculus

<400> SEQUENCE: 9

Met Glu Ser Gln Thr Gln Val Leu Ile Ser Leu Leu Phe Trp Val Ser
1               5                   10                  15

Gly Thr Cys Gly
            20
```